(12) United States Patent
Blinkovsky et al.

(10) Patent No.: US 6,664,092 B1
(45) Date of Patent: Dec. 16, 2003

(54) POLYPEPTIDES HAVING DIPEPTIDYL AMINOPEPTIDASE ACTIVITY AND NUCLEIC ACIDS ENCODING SAME

(75) Inventors: Alexander Blinkovsky, Davis, CA (US); Kimberly Brown, Elk Grove, CA (US); Michael W. Rey, Davis, CA (US); Alan Klotz, Dixon, CA (US); Tony Byun, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 337 days.

(21) Appl. No.: 09/079,592

(22) Filed: May 15, 1998

Related U.S. Application Data

(63) Continuation-in-part of application No. 08/857,884, filed on May 16, 1997, now abandoned.
(60) Provisional application No. 60/062,892, filed on Oct. 20, 1997.

(51) Int. Cl.[7] .............................. C12N 9/48; C07H 21/04
(52) U.S. Cl. ............... 435/212; 435/252.33; 435/254.3; 435/320.1; 536/23.2; 536/23.1; 536/23.74; 426/533; 426/549
(58) Field of Search ........................ 435/212, 6, 252.33, 435/254.3, 320.1; 536/23.2, 23.1, 23.74; 426/533, 549

(56) References Cited

FOREIGN PATENT DOCUMENTS

| WO | WO 94/25580 | * 11/1994 |
| WO | WO 96/28542 | 9/1996 |
| WO | WO 97/43910 | 11/1997 |

OTHER PUBLICATIONS

Tachi et al., "An X–Prolyl Dipeptidyl–Aminopeptidase From *Aspergillus oryzae*", Phytochemistry vol. 31, No. 11, pp. 3707–3709, 1992.
Beauvais et al., "Biochemical and Antigenic Characterization of a New Dipeptidyl–Peptidase Isolated From *Aspergillys fumigatus*" Journal of Biological Chemistry 272 (10), 1997, pp 6238–6244.
Heymann et al., "Complementary Action of Dipeptidyl Peptidase IV and Aminopeptidase M In The Digestion of β–Casein", J. Dairy Res 53, 1986, pp. 229–236.
Chemical Abstracts, vol. 124, No. 21, May 20, 1996 (XP–002051874).
Database WPI, Section Ch, Week 9527, May 9, 1995 (XP–002047737).
Database WPI, Section Ch, Week 9710, (XP–002076623) Nov. 17, 1993.
Beauvais et al., "Dipeptidyl–Peptidase IV Secreted by *Aspergillus fumigatus*, A Fungus Pathogenic to Humans" Infection and Immunity, vol. 65, No. 8, Aug. 1997, pp. 3042–3047.
EMBL/Genbank Databases, Accession No. AJ002369, Sequence Reference No. A0DPPIV, Mar. 2, 1998 (XP–002076626).

* cited by examiner

*Primary Examiner*—Nashaat T. Nashed
(74) *Attorney, Agent, or Firm*—Robert L. Starnes

(57) ABSTRACT

The present invention relates to isolated polypeptides having dipeptidyl aminopeptidase activity and isolated nucleic acid sequences encoding the polypeptides. The invention also relates to nucleic acid constructs, vectors, and host cells comprising the nucleic acid sequences as well as methods for producing and using the polypeptides.

26 Claims, 4 Drawing Sheets

ATGAGGTCGCTTTTGTGGGCTTGCTTGTTGCCGGGGCGTGTTGGCTGGGAGGGCGCTTGTTCGCCGATGAGTTCCCGAGGATATTCAG    90
M  R  S  L  L  W  A  S  L  L  S  G  V  L  A  G  R  A  L  V  S  P  D  E  F  P  E  D  I  Q

TTGGAAGATCTGCTGGAAGGATCCCAACAGCTTGAGGACTTCGCCTATGCCTACCCCGAGCGCAATCGCGTCTTTGGTGGTAAAGCCCAC  180
L  E  D  L  L  E  G  S  Q  Q  L  E  D  F  A  Y  A  Y  P  E  R  N  R  V  F  G  G  K  A  H

GACGACACGGTTAACTATCTCTACGAGAGCTGAAGAAGACTGGCTACTATGATGTCTACAAGCAGCCTCAGGTGCAGGTGTGGAGCAAT  270
D  D  T  V  N  Y  L  Y  E  E  L  K  K  T  G  Y  Y  D  V  Y  K  Q  P  Q  V  H  L  W  S  N

GCCGACCAGAGCTCAAGGTGGGCGATGAGGAAATCGAGGCGAAGACCATGACTTACAGTCCCAGTGAGGTCGAGGTCACCGCCGATGTAGCC  360
A  D  D  T  L  K  V  G  D  E  E  I  E  A  K  T  M  T  Y  S  P  S  V  E  V  T  A  D  V  A

GTCGTCAAGAACCTGGGATGCAGCGAGGCGGATTACCCATCCGATGTCGAGGGCGAAGCTCGCCCTGAGAGCGTGAGAATGCCCGTTC  450
V  V  K  N  L  G  C  S  E  A  D  Y  P  S  D  V  E  G  K  V  A  L  I  K  R  G  E  C  P  F

GGGGACAAGTCGGTTCTCGCTGCCAAAGCCGCCAAGGCCAAAGCCAAAGCCGCGGCTTCGGTTCTGGCCAAAGCCAAAGCCAAAGCCGCGGCTCGATTGTGTGGCCGGATCCATGGCGGGGCACCCTTGGC  540
G  D  K  S  V  L  A  A  K  A  K  A  A  A  S  I  V  Y  N  N  V  A  G  S  M  A  G  T  L  G

GCGGGGCGCAGAGTGATAAGGGACCGTATTCGGCCATTGTGTCGGAGGATGGCCAGAAGCTTGATCAAGCTTGCTGAGGCTGGA  630
A  A  Q  S  D  K  G  P  Y  S  A  I  V  G  I  S  L  E  D  G  Q  K  L  I  K  L  A  E  A  G

TCGGTATCTGTGGATCTGTGGGTGGATAGTAAGCAGGAGAACCGTACGACGTATAACGTTGTCGGCAGACGAAGGGCGGGGATCCGAAC  720
S  V  S  V  D  L  W  V  D  S  K  Q  E  N  R  T  T  Y  N  V  V  A  Q  T  K  G  G  D  P  N

AACGTCGTCGCGCTGGGTGGCCACACGGACTCAGTCGAGGCGGGCCCTGGTATCAACGACGATGGCTCGGGCATTATTAGCAACTTGGTC  810
N  V  V  A  L  G  G  H  T  D  S  V  E  A  G  P  G  I  N  D  D  G  S  G  I  I  S  N  L  V

FIG.1A

```
ATTGCCAAAGGCTCACGCAGTACTCCGTCAAGAATGCCGTGGCCTTCCTCTTCTGGACAGCAGAGGAGTTCGGTCTGTGGGCAGCAAC   900
 I  A  K  A  L  T  Q  Y  S  V  K  N  A  V  R  F  L  F  W  T  A  E  E  F  G  L  L  G  S  N

TACTACGTCTCCCATCTGAATGCCACGAGCTGAACAAGATCCGACTGTACCTGAACTTCGACATGATCGCCTCACCTAACTACGCCCTC   990
 Y  Y  V  S  H  L  N  A  T  E  L  N  K  I  R  L  Y  L  N  F  D  M  I  A  S  P  N  Y  A  L

ATGATCTATGACGGTGATGGGGATGGCTCGGCGTTCAACCAGAGCGGTTCCGGCCCAGATCGAGAAACTGTTCGAGGACTACTACGAC   1080
 M  I  Y  D  G  D  G  S  A  F  N  Q  S  G  P  A  G  S  A  Q  I  E  K  L  F  E  D  Y  Y  D

TCCATCGACCTGCCTCATATCCCCACCCAGTTTGACGGACGTTCCGACTACGAGGCCTTTATCCTGAACGGCATTCCGTCCGGTGGACTC   1170
 S  I  D  L  P  H  I  P  T  Q  F  D  G  R  S  D  Y  E  A  F  I  L  N  G  I  P  S  G  G  L

TTCACGGGGCGCCGAGGGCATCATGTCCGAAGAGAACGCCAAGCGCTGGGGAGGTCAAGCCGGCGTGGCCTACGACGCCAACTACCACGCC   1260
 F  T  G  A  E  G  I  M  S  E  E  N  A  S  R  W  G  G  Q  A  G  V  A  Y  D  A  N  Y  H  A

GCGGGAGACAACATGACCAACCTCAACCATGAAGCCTTCCTGATCAACTCCAAAGCCACCGCCTTCGCCGTCGCCACTTACGCCAACGAC   1350
 A  G  D  N  M  T  N  L  N  H  E  A  F  L  I  N  S  K  A  T  A  F  A  V  A  T  Y  A  N  D

CTCTCCTCGATCCCCAAACGGAATACCACATCCTCCTTGCACCGAGAGCCGAAGAGAGCTCCGAAGACA   1440
 L  S  S  I  P  K  R  N  T  T  S  S  L  H  R  R  A  R  T  M  R  P  F  G  K  R  A  P  K  T

CACGGCTCACGTATCAGGATCCGGATGCTGGCATTCTCAAGTCGAGGCATAG  1491
 H  A  H  V  S  G  S  G  C  W  H  S  Q  V  E  A
```

POLYPEPTIDES HAVING DIPEPTIDYL AMINOPEPTIDASE ACTIVITY AND NUCLEIC ACIDS ENCODING SAME

CROSS-REFERENCE TO RELATED APPLICATIONS

This application is a continuation-in-part of U.S. application Ser. No. 08/857,884 filed on May 16, 1997, now abandoned, and claim benefit from provisional U.S. application Ser. No. 60/062,892 filed on Oct. 20, 1997, which applications are fully incorporated herein by reference.

BACKGROUND OF THE INVENTION

1. Field of the Invention

The present invention relates to polypeptides having dipeptidyl aminopeptidase activity and isolated nucleic acid sequences encoding the polypeptides. The invention also relates to nucleic acid constructs, vectors, and host cells comprising the nucleic acid sequences as well as methods for producing the polypeptides. The present invention further relates to methods of obtaining protein hydrolysates useful as flavour improving agents.

2. Description of the Related Art

Various food products, e.g., soups, sauces and seasonings, contain flavoring agents obtained by hydrolysis of proteinaceous materials. This hydrolysis is conventionally accomplished using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Increasing concern over the use of flavoring agents obtained by chemical hydrolysis has led to the development of enzymatic hydrolysis processes.

Enzymatic hydrolysis processes of proteinaceous materials aim at obtaining a high degree of hydrolysis (DH), and this is usually attained using a complex of unspecific acting proteolytic enzymes (i.e., unspecific-acting endo- and exopeptidases). For example, WO 94/25580 describes a method for hydrolyzing proteins by use of an unspecific acting enzyme preparation obtained from *Aspergillus oryzae*. Specific acting proteolytic enzymes have not been used for this purpose because such enzymes only lead to an inadequate degree of hydrolysis.

Polypeptides having dipeptidyl aminopeptidase activity catalyze the removal of dipeptides from the N-terminus of peptides, polypeptides, and proteins. Such polypeptides are classified under the Enzyme Classification Number E.C. 3.4.14.—of the International Union of Biochemistry and Molecular Biology.

Beauvais et al. (1997, *Journal of Biological Chemistry* 272: 6238–6244) disclose a dipeptidyl-peptidase from *Aspergillus fumigatus* which has a molecular weight of 88 kDa by SDS-PAGE and a substrate specificity limited to the hydrolysis of X-Ala, His-Ser, and Ser-Tyr dipeptides at a neutral pH optimum. Tachi et al. (1992, *Phytochemistry* 31: 3707–3709) disclose an X-prolyl dipeptidyl aminopeptidase from *Aspergillus oryzae* which has a molecular weight of 145 kDa by SDS-PAGE and a substrate specificity toward the peptide bond at the carboxyl site of a proline residue in the penultimate position of N-terminal free dipeptides and amides at a neutral pH optimum.

The production of protein hydrolysates with desirable organoleptic properties and high degrees of hydrolysis generally requires the use of a mixture of peptidase activities. It would be desirable to provide a single component peptidase enzyme which has activity useful for improving the organoleptic properties and degree of hydrolysis of protein hydrolysates used in food products either alone or in combination with other enzymes.

It is an object of the present invention to provide improved polypeptides having dipeptidyl aminopeptidase activity as well as methods for obtaining protein hydrolysates with desirable organoleptic qualities and high degrees of hydrolysis.

SUMMARY OF THE INVENTION

The present invention relates to isolated polypeptides having dipeptidyl aminopeptidase activity selected from the group consisting of:
(a) a polypeptide having an amino acid sequence which has at least 50% identity with the amino acid sequence of SEQ ID NO:2;
(b) a polypeptide encoded by a nucleic acid sequence which hybridizes under medium stringency conditions with (i) the nucleic acid sequence of SEQ ID NO: 1, (ii) its complementary strand, or (iii) a subsequence thereof;
(c) an allelic variant of (a) or (b); and
(d) a fragment of (a), (b), or (c), wherein the fragment has dipeptidyl aminopeptidase activity; and
(e) a polypeptide having dipeptidyl aminopeptidase activity with physicochemical properties of (i) a pH optimum in the range of from about pH 4.4 to about pH 9.8 determined after incubation for 5 minutes at ambient temperature in the presence of Ala-Pro-para-nitroanilide; (ii) a temperature stability of 90% or more, relative to initial activity, at pH 7.5 determined after incubation for 20 minutes at 65° C. in the absence of substrate; and (iii) an activity towards Xaa-Pro-para-nitroanilide or Xaa-Ala-para-nitroanilide wherein Xaa is selected from the group consisting of Ala, Arg, Asp, Gly, and Val.

The present invention also relates to isolated nucleic acid sequences encoding the polypeptides and to nucleic acid constructs, vectors, and host cells comprising the nucleic acid sequences as well as methods for producing the polypeptides.

The present invention also relates to methods for obtaining hydrolysates from proteinaceous substrates which comprise subjecting the proteinaceous material to a polypeptide with dipeptidyl aminopeptidase activity alone or in combination with an endopeptidase, and to hydrolysates obtained from the method.

The present invention also relates to methods for obtaining from a proteinaceous substrate a hydrolysate enriched in free glutamic acid and/or peptide bound glutamic acid residues, which methods comprise subjecting the substrate to a deamidation process and to the action of a polypeptide having dipeptidyl aminopeptidase activity.

The present invention further relates to flavor-improving compositions comprising a polypeptide with dipeptidyl aminopeptidase activity.

In a final aspect, the methods of the invention may be used in food related applications to improve flavor, such as baking. Alternatively, flavor improvement in foods may be achieved by the addition of hydrolysates obtained by the methods of the invention.

BRIEF DESCRIPTION OF THE FIGURES

FIGS. 1A and 1B show the nucleic acid sequence and the deduced amino acid sequence of an *Aspergillus oryzae*

ATCC 20386 dipeptidyl aminopeptidase (SEQ ID NOS:1 and 2, respectively).

Figure 2:
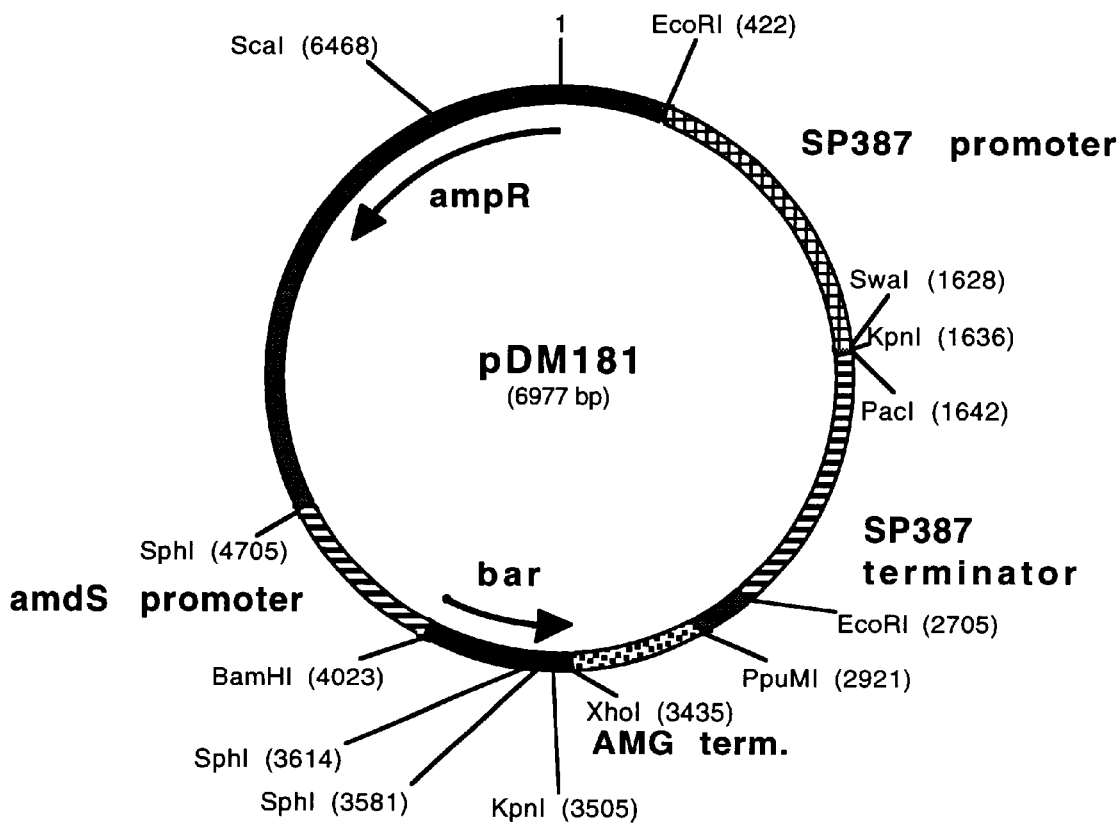

FIG. 2 shows a restriction map of pDM181.

Figure 3:
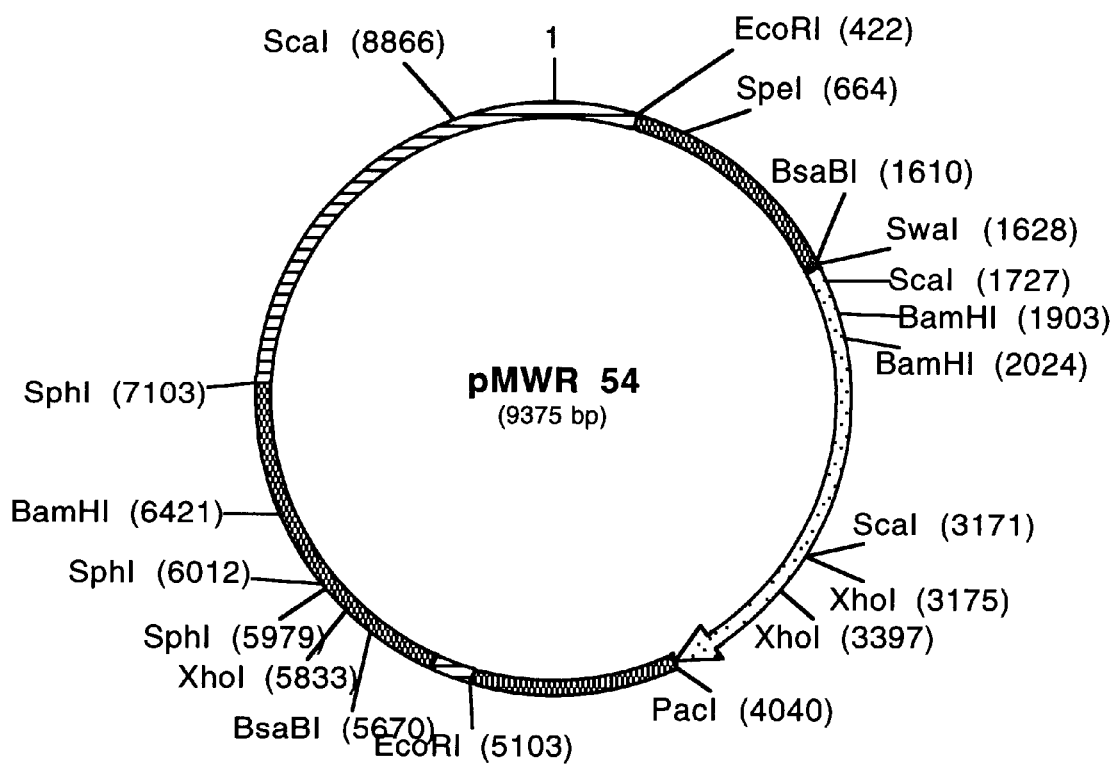

FIG. 3 shows a restriction map of pMWR54.

DETAILED DESCRIPTION OF THE INVENTION

Polypeptides having Dipeptidyl Aminopeptidase Activity

The term "dipeptidyl aminopeptidase activity" is defined herein as a peptidase activity which cleaves dipeptides from the N-terminal end of a peptide, polypeptide, or protein sequence. Defined in a general manner, the dipeptidyl aminopeptidase is capable of cleaving the dipeptide XY from the unsubstituted N-terminal amino group of a peptide, polypeptide, or protein, wherein X or Y may represent any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val, but at least Ala, Arg, Asp, Gly, and/or Val. All of X and Y may be different or identical. It will be understood that the isolated polypeptides having dipeptidyl aminopeptidase activity of the present invention may be unspecific as to the amino acid sequence of the dipeptide to be cleaved.

In a first embodiment, the present invention relates to isolated polypeptides having an amino acid sequence which has a degree of identity to the amino acid sequence of SEQ ID NO:2 of at least about 50%, preferably at least about 60%, preferably at least about 70%, more preferably at least about 80%, even more preferably at least about 90%, most preferably at least about 95%, and even most preferably at least about 97%, which have dipeptidyl aminopeptidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two amino acid sequences is determined by the Clustal method (Higgins, 1989, *CABIOS* 5: 151–153) with an identity table, a gap penalty of 10, and a gap length penalty of 10.

Preferably, the polypeptides of the present invention comprise the amino acid sequence of SEQ ID NO:2 or an allelic variant; and a fragment thereof, wherein the fragment has dipeptidyl aminopeptidase activity. In a more preferred embodiment, the polypeptides of the present invention comprise the amino acid sequence of SEQ ID NO:2. In another preferred embodiment, the polypeptide of the present invention has the amino acid sequence of SEQ ID NO:2 or a fragment thereof, wherein the fragment has dipeptidyl aminopeptidase activity. A fragment of SEQ ID NO:2 is a polypeptide having one or more amino acids deleted from the amino and/or carboxy terminus of this amino acid sequence. In a most preferred embodiment, the polypeptide has the amino acid sequence of SEQ ID NO:2.

Preferably, a fragment contains at least 455 amino acid residues, more preferably at least 555 amino acid residues, and most preferably at least 655 amino acid residues.

An allelic variant denotes any of two or more alternative forms of a gene occupying the same chomosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used to denote a protein encoded by an allelic variant of a gene.

The amino acid sequences of the homologous polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having dipeptidyl aminopeptidase activity which are encoded by nucleic acid sequences which hybridize under low stringency conditions, more preferably medium stringency conditions, and most preferably high stringency conditions, with an oligonucleotide probe which hybridizes under the same conditions with the nucleic acid sequence of SEQ ID NO:1 or its complementary strand (J. Sambrook, E. F. Fritsch, and T. Maniatus, 1989, *Molecular Cloning, A Laboratory Manual*, 2d edition, Cold Spring Harbor, N.Y.); or allelic variants and fragments of the polypeptides, wherein the fragments have dipeptidyl aminopeptidase activity.

Hybridization indicates that the nucleic acid sequence hybridizes to the oligonucleotide probe corresponding to the polypeptide encoding part of the nucleic acid sequence shown in SEQ ID NO:1, under low to high stringency conditions (i.e., prehybridization and hybridization at 42° C. in 5×SSPE, 0.3% SDS, 200 µg/ml sheared and denatured salmon sperm DNA, and either 25, 35 or 50% formamide for low, medium and high stringencies, respectively), following standard Southern blotting procedures.

The amino acid sequence of SEQ ID NO:2 or a partial sequence thereof may be used to design an oligonucleotide probe, or a nucleic acid sequence encoding a polypeptide of the present invention, such as the nucleic acid sequence of SEQ ID NO:1, or a subsequence thereof, may be used to identify and clone DNA encoding polypeptides having dipeptidyl aminopeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin).

Thus, a genomic, cDNA or combinatorial chemical library prepared from such other organisms may be screened for DNA which hybridizes with the probes described above and which encodes a polypeptide having dipeptidyl aminopeptidase activity. Genomic or other DNA from such other organisms may be separated by agarose or polyacrylarmide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, the carrier material is used in a Southern blot in which the carrier material is finally washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C. Molecules to which the oligonucleotide probe hybridizes under these conditions are detected using X-ray film.

In a third embodiment, the present invention relates to isolated polypeptides having the following physicochemical properties: (a) a pH optimum in the range of from about pH 4.4 to about pH 9.8 determined after incubation for 5 minutes at ambient temperature in the presence of Ala-Pro-para-nitroanilide; (b) a temperature stability of 90% or more, relative to initial activity, at pH 7.5 determined after incubation for 20 minutes at 65° C. in the absence of substrate; and (c) an activity towards Xaa-Pro-para-nitroanilide or Xaa-Ala-para-nitroanilide wherein Xaa is selected from the group consisting of Ala, Arg, Asp, Gly, and Val. The polypeptides of the present invention also have the ability to hydrolyze other substrates.

In a preferred embodiment, the pH optimum in the range of from about pH 4.4 to about pH 9.8, more preferably in the range of from about pH 5.8 to about pH 9.8, and most preferably in the range of from about pH 7.5 to about pH 9.3 determined after incubation for 5 minutes at ambient temperature in the presence of Ala-Pro-para-nitroanilide.

In another preferred embodiment, a polypeptide of the present invention acts synergistically with an aminopeptidase to hydrolyze another polypeptide. The term "acts synergistically with an aminopeptidase to hydrolyze another polypeptide" is defined herein as the combination of a dipeptidyl aminopeptidase and an aminopeptidase which increases at least 5-fold, more preferably at least 10-fold, even more preferably at least 25-fold, most preferably at least 50-fold, and even most preferably at least 100-fold the hydrolysis of a peptide or a polypeptide relative to either individual enzyme alone. The aminopeptidase may be any aminopeptidase, but is preferably an aminopeptidase obtained from *Aspergillus oryzae*, and more preferably aminopeptidase I obtained from *Aspergillus oryzae* as described in WO 96/28542. The polypeptide is preferably a tripeptide, but may be any larger peptide or protein.

In a fourth embodiment, the present invention relates to isolated polypeptides having immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

Polypeptides encoded by nucleic acid sequences which hybridize with an oligonucleotide probe which hybridizes with the nucleic acid sequence of SEQ ID NO:1, its complementary strand, or allelic variants and subsequences of SEQ ID NO:1; allelic variants and fragments of the polypeptides; or the homologous polypeptides and polypeptides having identical or partially identical immunological properties may be obtained from microorganisms of any genus.

In a preferred embodiment, these polypeptides may be obtained from a bacterial source.

For example, these polypeptides may be obtained from a gram positive bacterium such as a Bacillus strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis*; or a Streptomyces strain, e.g., *Streptomyces lividans* or *Streptomyces murinus*; or from a gram negative bacterium, e.g., *E. coli* or Pseudomonas sp.

The polypeptides may be obtained from a fungal source, and more preferably from a yeast strain such as a Candida, Kluyveromyces, Pichia, Saccharomyces, Schizosaccharomyces, or Yarrowia strain; or a filamentous fungal strain such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypociadium, or Trichoderma strain.

In a preferred embodiment, the polypeptides are obtained from a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

In another preferred embodiment, the polypeptides are obtained from a *Fusarium bactridioides, Fusarium cereals, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

The polypeptides of the present invention are preferably obtained from species of Aspergillus including, but not limited to, *Aspergillus aculeatus, Aspergillus awamori, Aspergillus foetidus, Aspergillus japonicus, Aspergillus nidulans, Aspergillus niger,* or *Aspergillus oryzae.*

In a more preferred embodiment, a polypeptide of the present invention is obtained from an *Aspergillus oryzae* strain, and most preferably from *Aspergillus oryzae* ATCC 20386 or a mutant strain thereof, e.g., the polypeptide with the amino acid sequence of SEQ ID NO:2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. The polypeptides of the present invention may also be obtained from microorganisms which are synonyms of Aspergillus as defined by Raper, K. D. and Fennel, D. I., 1965, *The Genus Aspergillus,* The Wilkins Company, Baltimore. Aspergilli are mitosporic fungi characterized by an aspergillum conprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of Aspergillus include Eurotium, Neosartorya, and Emericella. Strains of Aspergillus and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding the polypeptide has been detected with the probe(s), the sequence may be isolated or cloned by utilizing techniques which are known to those of ordinary skill in the art (see, e.g., Sambrook et al., 1989, supra).

For purposes of the present invention, the term "obtained from" as used herein in connection with a given source shall mean that the polypeptide is produced by the source or by a cell in which a gene from the source has been inserted.

As defined herein, an "isolated" polypeptide is a polypeptide which is essentially free of other non-dipeptidyl aminopeptidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Nucleic Acid Sequences

The present invention also relates to isolated nucleic acid sequences which encode a polypeptide of the present invention. In a preferred embodiment, the nucleic acid sequence encodes a polypeptide obtained from Aspergillus, e.g., *Aspergillus oryzae,* and in a more preferred embodiment, the nucleic acid sequence is obtained from *Aspergillus oryzae* ATCC 20386, e.g., the nucleic acid sequence of SEQ ID NO:1. In another more preferred embodiment, the nucleic acid sequence is the sequence contained in plasmid pMWR52 which is contained in *Escherichia coli* NRRL B-21682. The present invention also encompasses nucleic acid sequences which encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 which have dipeptidyl aminopeptidase activity. A subsequence of SEQ ID NO:1 is a nucleic acid sequence encompassed by SEQ ID NO:1 except that one or more nucleotides from the 5' end and/or 3' end have been deleted. Preferably, a subsequence contains at least 990 nucleotides, more preferably at least 1140 nucleotides, and most preferably at least 1290 nucleotides.

The nucleic acid sequences may be obtained from microorganisms which are taxonomic equivalents of Aspergillus as defined by Raper, K. D. and Fennel, D. I., 1965, supra., regardless of the species name by which they are known.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Aspergillus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the nucleic acid sequence of SEQ ID NO:1 of at least about 50%, preferably about 60%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Clustal method (Higgins, 1989, supra) with an identity table, a gap penalty of 10, and a gap length penalty of 10.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for dipeptidyl aminopeptidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

The present invention also relates to isolated nucleic acid sequences encoding a polypeptide of the present invention, which hybridize under low stringency conditions, more preferably medium stringency conditions, and most preferably high stringency conditions, with an oligonucleotide probe which hybridizes under the same conditions with the nucleic acid sequence of SEQ ID NO:1 or its complementary strand; or allelic variants and subsequences thereof (Sambrook et al., 1989, supra).

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (U.S. Pat. No. 4,288,627), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral alpha-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL 1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423–488. In a mammalian host cell, useful promoters include viral promoters such as those from Simian Virus 40 (SV40), Rous sarcoma virus (RSV), adenovirus, bovine papilloma virus (BPV), and human cytomegalovirus (CMV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase. Useful polyadenylation sequences for yeast host cells are described by Guo and Sherman, 1995, *Molecular Cellular Biology* 15: 5983–5990. Polyadenylation sequences are well known in the art for mammalian host cells.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. The signal peptide coding region may be obtained from a glucoamylase or an amylase gene from an Aspergillus species, a lipase or proteinase gene from a Rhizomucor species, the gene for the alpha-factor from Saccharomyces cerevisiae, an amylase or a protease gene from a Bacillus species, or the calf prepro-chymosin gene. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the Bacillus stearothermophilus alpha-amylase gene, the Bacillus licheniformis subtilisin gene, the Bacillus licheniformis beta-lactamase gene, the Bacillus stearothermophilus neutral proteases genes (nprT, nprS, nprM), or the Bacillus subtilis PrsA gene. Further signal peptides are described by Simonen and Palva, 1993, Microbiological Reviews 57: 109–137.

An effective signal peptide coding region for filamentous fungal host cells is the signal peptide coding region obtained from the Aspergillus oryzae TAKA amylase gene, Aspergillus niger neutral amylase gene, Rhizomucor miehei aspartic proteinase gene, Humicola lanuginosa cellulase gene, or Humicola lanuginosa lipase gene.

Useful signal peptides for yeast host cells are obtained from the genes for Saccharomyces cerevisiae alpha-factor and Saccharomyces cerevisiae invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the Bacillus subtilis alkaline protease gene (aprE), the Bacillus subtilis neutral protease gene (nprT), the Saccharomyces cerevisiae alpha-factor gene, the Rhizomucor miehei aspartic proteinase gene, or the Myceliophthora thermophila laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

The nucleic acid constructs of the present invention may also comprise one or more nucleic acid sequences which encode one or more factors that are advantageous for directing the expression of the polypeptide, e.g., a transcriptional activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

A transcriptional activator is a protein which activates transcription of a nucleic acid sequence encoding a polypeptide (Kudla et al., 1990, EMBO Journal 9: 1355–1364; Jarai and Buxton, 1994, Current Genetics 26: 2238–244; Verdier, 1990, Yeast 6: 271–297). The nucleic acid sequence encoding an activator may be obtained from the genes encoding Bacillus stearothermophilus NprA (nprA), Saccharomyces cerevisiae heme activator protein 1 (hap1), Saccharomyces cerevisiae galactose metabolizing protein 4 (gal4), Aspergillus nidulans amnonia regulation protein (areA), and Aspergillus oryzae alpha-amylase activator (amyR). For further examples, see Verdier, 1990, supra and MacKenzie et al., 1993, Journal of General Microbiology 139: 2295–2307.

A chaperone is a protein which assists another polypeptide in folding properly (Hartl et al., 1994, TIBS 19: 20–25; Bergeron et al., 1994, TIBS 19: 124–128; Demolder et al., 1994, Journal of Biotechnology 32: 179–189; Craig, 1993, Science 260: 1902–1903; Gething and Sambrook, 1992, Nature 355: 33–45; Puig and Gilbert, 1994, Journal of Biological Chemistry 269: 7764–7771; Wang and Tsou, 1993, The FASEB Journal 7: 1515–11157; Robinson et al., 1994, Bio/Technology 1: 381–384; Jacobs et al., 1993, Molecular Microbiology 8: 957–966). The nucleic acid sequence encoding a chaperone may be obtained from the genes encoding Bacillus subtilis GroE proteins, Bacillus subtilis PrsA, Aspergillus oryzae protein disulphide isomerase, Saccharomyces cerevisiae calnexin, Saccharomyces cerevisiae BiP/GRP78, and Saccharomyces cerevisiae Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, Yeast 10: 67–79; Fuller et al., 1989, Proceedings of the National Academy of Sciences USA 86: 1434–1438; Julius et al., 1984, Cell 37: 1075–1089; Julius et al., 1983, Cell 32: 839–852; U.S. Pat. No. 5,702, 934). The nucleic acid sequence encoding a processing protease may be obtained from the genes encoding Saccharomyces cerevisiae dipeptidyl aminopeptidase, Saccharomyces cerevisiae Kex2, Yarrowia lipolytica dibasic processing endoprotease (xpr6), and Fusarium oxysporum metalloprotease (p45 gene).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, Aspergillus niger glucoamylase promoter, and the Aspergillus oryzae glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon.

Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for mammalian cells are the dihydrofolate reductase (dfhr), hygromycin phosphotransferase (hygB), aminoglycoside phosphotransferase II, and phleomycin resistance genes. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents from other species. Preferred for use in an Aspergillus cell are the amdS and pyrG genes of *Aspergillus nidulans* or *Aspergillus oryzae* and the bar gene of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB 110, pE 194, pTA 1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by culturing the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

A vector comprising a nucleic acid sequence of the present invention is introduced into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis, and Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus,* or *Bacillus subtilis* cell. The introduction of a vector into a bacterial host cell may, for instance, be effected by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see, e.g., Koehler and Thorne, 1987, *Journal of Bacteriology* 169: 5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al, 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achlya. Examples of mitosporic fungi include Aspergillus, Penicillium, Candida, and Alternaria. Representative groups of Zygomycota include, e.g., Rhizopus and Mucor.

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e.g., genera Kluyveromyces, Pichia, and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sporobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast, Bacil*, M., Horecker, B. J., and Stopani, A. O. M., editors, 2nd edition, 3s 1987; The Yeasts, Rose, A. H., and Harrison, J. S., editors, 2nd edition, 1987; and *The Molecular Biology of the Yeast Saccharomyces*, Strathern et al., editors, 1981).

In an even more preferred embodiment, the yeast host cell is a cell of a species of Candida, Hansenula, Kluyveromyces, Pichia, Saccharomyces, Schizosaccharomyces, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergillus nidulans, Aspergillus niger*, or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474 Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. Mammalian cells may be transformed by direct uptake using the calcium phosphate precipitation method of Graham and Van der Eb (1978, *Virology* 52: 546).

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Aspergillus.

The present invention also relates to methods for producing a polypeptide of the present invention comprising (a) cultivating a host cell under conditions conducive for production of the polypeptide; and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670. Gene activation technology is based on activating a gene which is normally unexpressed in a cell or increasing expression of a gene which is expressed at very low levels in a cell. Gene activation technology includes methods of inserting an exogenous DNA construct containing a regulatory sequence, an exon, and/or a splice donor site into the genomic DNA of a cell in such a manner that the insertion results in the production of a new transcription unit in which the regulatory sequence, the exon, and/or the splice donor site are operably linked to and activate expression of the endogenous gene.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, California, 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining dipeptidyl aminopeptidase activity are known in the art and include, e.g., measuring the initial rate of hydrolysis of a p-nitroanilide at 405 nm.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing, differential solubility (e.g., ammonium sulfate precipitation), SDS-PAGE, or extraction (see, e.g.,*Protein Purification*, J. -C. Janson and Lars Ryden, editors, VCH Publishers, New York, 1989).

Removal or Reduction of Dipeptidyl Aminopeptidase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell.

The construction of strains which have reduced dipeptidyl aminopeptidase activity may be conveniently accomplished by modification or inactivation of a nucleic acid sequence necessary for expression of the polypeptide having dipeptidyl aminopeptidase activity in the cell. The nucleic acid sequence to be modified or inactivated may be, for example, a nucleic acid sequence encoding the polypeptide or a part thereof essential for exhibiting dipeptidyl aminopeptidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification include, but are not limited to, a leader, a polyadenylation sequence, a propeptide sequence, a signal sequence, and a termination terminator.

Modification or inactivation of the nucleic acid sequence may be performed by subjecting the cell to mutagenesis and selecting for cells in which the dipeptidyl aminopeptidase producing capability has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced or no expression of dipeptidyl aminopeptidase activity.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art.

Although, in principle, the modification may be performed in vivo, i.e., directly on the cell expressing the nucleic acid sequence to be modified, it is preferred that the modification be performed in vitro as exemplified below.

An example of a convenient way to inactivate or reduce production by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence encoding a polypeptide of the present invention may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention relates to a method for producing a protein product essentially free of dipeptidyl aminopeptidase activity by fermentation of a cell which produces both a polypeptide of the present invention as well as the protein product of interest.

The method comprises adding an effective amount of an agent capable of inhibiting dipeptidyl aminopeptidase activity to the fermentation broth either during or after the fermentation has been completed, recovering the product of interest from the fermentation broth, and optionally subjecting the recovered product to further purification.

In a still further alternative aspect, the present invention relates to a method for producing a protein product essentially free of dipeptidyl aminopeptidase activity, wherein the protein product of interest is encoded by a DNA sequence present in a cell encoding a polypeptide of the present invention. The method comprises cultivating the cell under conditions permitting the expression of the product, subjecting the resultant culture broth to a combined pH and temperature treatment so as to reduce the dipeptidyl aminopeptidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a dipeptidyl aminopeptidase inhibitor.

The combined pH and temperature treatment is preferably carried out at a pH in the range of 9–11 and a temperature in the range of 40–75° C. for a sufficient period of time to attain the desired effect, where typically, 30 to 60 minutes is sufficient.

In accordance with this aspect of the invention, it is possible to remove at least 60%, preferably at least 75%, more preferably at least 85%, still more preferably at least 95%, and most preferably at least 99% of the dipeptidyl aminopeptidase activity. It is contemplated that a complete removal of dipeptidyl aminopeptidase activity may be obtained by use of these methods.

The methods used for cultivation and purification of the product of interest may be performed by methods known in the art.

The methods of the present invention for producing an essentially dipeptidyl aminopeptidase-free product is of particular interest in the production of eukaryotic polypeptides, in particular fungal proteins such as enzymes. The enzyme may be selected from, e.g., an amylolytic enzyme, a lipolytic enzyme, a proteolytic enzyme, a cellulytic enzyme, an oxidoreductase or a plant cell-wall degrading enzyme. Examples of such enzymes include an aminopeptidase, an amylase, an amyloglucosidase, a carbohydrase, a carboxypeptidase, a catalase, a cellulase, a chitinase, a cutinase, a cyclodextrin glycosyltransferase, a deoxyribonuclease, an esterase, a galactosidase, a beta-galactosidase, a glucoamylase, a glucose oxidase, a glucosidase, a haloperoxidase, a hemicellulase, an invertase, an isomerase, a laccase, a ligase, a lipase, a lyase, a mannosidase, an oxidase, a pectinolytic enzyme, a peroxidase, a phytase, a phenoloxidase, a polyphenoloxidase, a proteolytic enzyme, a ribonuclease, a transferase, a transglutaminase, or a xylanase. The dipeptidyl aminopeptidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from dipeptidyl aminopeptidase activity which is produced by a method of the present invention.

Methods of Producing Protein Hydrolysates

The polypeptides of the present invention may be used in the production of protein hydrolysates for enhancing the degree of hydrolysis and flavor development.

The present invention further relates to methods for using a polypeptide of the present invention in combination with an endopeptidase to produce a high degree of hydrolysis of a protein-rich material. The method comprises treating of a proteinaceous substrate with the polypeptide and an endopeptidase. The substrate may be treated with the enzymes concurrently or consecutively.

A polypeptide of the present invention is added to the proteinaceous substrate in an effective amount conventionally employed in protein hydrolysis processes, preferably in the range of from about 0.1 to about 100,000 dipeptidyl aminopeptidase units (DPAPU) per 100 g of protein, and more preferably in the range of from about 1 to about 10,000 dipeptidyl aminopeptidase units per 100 g of protein. As defined herein, one dipeptidyl aminopeptidase Unit (DPAPU) is the amount of enzyme needed to release 1 micromole of p-nitroanilide per minute from Ala-Pro-p-nitroanilide (Sigma Chemical Co., St. Louis Mo.) under specified conditions.

The endopeptidase may be obtained from a strain of Bacillus, preferably *Bacillus licheniformis* or *Bacillus subtilis*, a strain of Staphylococcus, preferably *Staphylococcus aureus*, a strain of Streptomyces, preferably *Streptomyces thermovularis* or *Streptomyces griseus*, a strain of Actinomyces species, a strain of Aspergillus, preferably *Aspergillus aculeatus, Aspergillus awamori, Aspergillus foetidus, Aspergillus nidulans, Aspergillus niger*, or *Aspergillus oryzae*, or a strain of Fusarium, preferably *Fusarium venenatum*.

The endopeptidase is added to the proteinaceous substrate in an effective amount conventionally employed in protein hydrolysis processes, preferably in the range of from about 0.05 to about 15 AU/100 g of protein, and more preferably from about 0.1 to about 8 AU/100 g of protein. One AU (Anson Unit) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milli-equivalent of tyrosine. The analytical method AF 4/5 is available upon request from Novo Nordisk A/S, Denmark, which is incorporated herein by reference.

The enzymatic treatment, i.e., the incubation of the substrate with the enzyme preparations, may take place at any convenient temperature at which the enzyme preparation does not become inactivated, preferably in the range of from about 20° C. to about 70° C. In accordance with established practice, the enzyme preparations may be suitably inactivated by increasing the temperature of the incubation mixture to a temperature where the enzymes become inactivated, e.g., to above about 70° C., or similarly by decreasing the pH of the incubation mixture to a point where the enzymes become inactivated, e.g., below about 4.0.

Furthermore, the methods of the present invention result in enhancement of the degree of hydrolysis of a proteinaceous substrate. As used herein, the degree of hydrolysis (DH) is the percentage of the total number of amino bonds in a protein that has been hydrolyzed by a proteolytic enzyme.

In another aspect of the present invention, the hydrolysates have an increased content of Ala, Arg, Asp, Gly, and/or Val, e.g., 1.1 times greater.

In another aspect of the present invention, a polypeptide of the present invention acts synergistically with an aminopeptidase to hydrolyze a tripeptide where either enzyme activity alone does not hydrolyze the tripeptide. In a preferred embodiment, the aminopeptidase is aminopeptidase I obtained from *Aspergillus oryzae* as described in WO 96/28542.

The present invention also relates to methods for obtaining a protein hydrolysate enriched in free glutamic acid and/or peptide bound glutamic acid residues, which method comprises:
 (a) subjecting the substrate to a deamidation process; and
 (b) subjecting the substrate to the action of a polypeptide having dipeptidyl aminopeptidase activity.

The two steps may be performed simultaneously, or the second step may be performed subsequent to the first step.

These methods of the present invention produce protein hydrolysates of excellent flavor because glutamic acid (Glu), whether free or peptide bound, plays an important role in the flavor and palatability of protein hydrolysates. These method also produce protein hydrolysates having improved functionality, in particular, improved solubility, improved emulsifying properties, increased degree of hydrolysis, and improved foaming properties.

The conversion of amides (glutamine or asparagine) into charged acids (glutamic acid or aspartic acid) via the liberation of ammonia is known as deamidation. Deamidation may take place as a non-enzymatic or as an enzymatic deamidation process.

In a preferred embodiment, the deamidation is carried out as an enzymatic deamidation process, e.g., by subjecting the substrate to a transglutaminase and/or peptidoglutaminase.

The transglutaminase may be of any convenient source including mammals, see e.g., JP 1050382 and JP 5023182, including activated Factor XIII, see e.g., WO 93/15234; those derived from fish, see e.g., EP 555,649; and those obtained from microorganisms, see e.g., EP 379,606, WO 96/06931 and WO 96/22366. In a preferred embodiment, the transglutaminase is obtained from an Oomycete, including a strain of Phytophthora, preferably *Phytophthora cactorum*, or a strain of Pythium, preferably *Pythium irregulare*, *Pythium sp., Pythium intermedium, Pythium ultimum*, or *Pythium periilum* (or *Pythium periplocum*). In another preferred embodiment, the transglutaminase is of bacterial origin and is obtained from a strain of Bacillus, preferably *Bacillus subtilis*, a strain of Streptoverticillium, preferably *Streptoverticillium mobaraensis, Streptoverticillium griseocarneum*, or *Streptoverticillium cinnamoneum*, and a strain of Streptomyces, preferably *Streptomyces lydicus*.

The peptidoglutaminase may be a peptidoglutaminase I (peptidyl-glutaminase; EC 3.5.1.43), or a peptidoglutaminase II (protein-glutamine glutaminase; EC 3.5.1.44), or any mixture thereof. The peptidoglutaminase may be obtained from a strain of Aspergillus, preferably *Aspergillus japonicus*, a strain of Bacillus, preferably *Bacillus circulans*, a strain of Cryptococcus, preferably *Cryptococcus albidus*, or a strain of Debaryomyces, preferably *Debaryomyces kloecheri*.

The transglutaminase is added to the proteinaceous substrate in an effective amount conventionally employed in deamidation processes, preferably in the range of from about 0.01 to about 5% (w/w), and more preferably in the range of from about 0.1 to about 1% (w/w) of enzyme preparation relating to the amount of substrate.

The peptidoglutaminase is added to the proteinaceous substrate in an effective amount conventionally employed in deamidation processes, preferably in the range of from about 0.01 to about 100,000 PGase Units per 100 g of substrate, and more preferably in the range of from about 0.1 to about 10,000 PGase Units per 100 g of substrate.

The peptidoglutaminase activity may be determined according to the procedure of Cedrangoro et al (1965, *Enzymologia* 29: 143). According to this procedure, 0.5 ml of an enzyme sample, adjusted to pH 6.5 with I N NaOH, is charged into a small vessel. Then 1 ml of a borate pH 10.8 buffer solution is added to the vessel. The discharged ammonia is absorbed by 5 N sulphuric acid, and by use of Nessler's reagent the mixture is allowed to form color which is measured at 420 nm. One PGase unit is the amount of enzyme capable of producing 1 micromole of ammonia per minute under these conditions.

Alternatively, the peptidoglutaminase activity may be determined according to the procedure described in U.S. Pat No. 3,857,967 or Example 17 below.

In step (b) of the methods of the present invention, the substrate is subjected to a polypeptide of the present invention. A polypeptide of the present invention is added to the proteinaceous substrate in an effective amount conventionally employed in protein hydrolysis processes, preferably in the range of from about 0.001 to about 0.5 AU/100 g of substrate, more preferably in the range of from about 0.01 to about 0.1 AU/100 g of substrate.

In another embodiment, the methods of the present invention may be used to produce a hydrolysate enriched in free glutamic acid and/or peptide bound glutamic acid residues further comprise:

(c) subjecting the substrate to one or more unspecific acting endo- and/or exo-peptidase enzymes.

This step may take place simultaneously with steps (a) and (b), or may follow steps (a) and (b).

In a preferred embodiment, the unspecific acting endo- and/or exo-peptidase enzyme is obtained from a strain of Aspergillus, preferably *Aspergillus niger, Aspergillus oryzae*, or *Aspergillus sojae*, or a strain of Bacillus, preferably *Bacillus amyloliquefaciens, Bacillus lentus, Bacillus licheniformis*, or *Bacillus subtilis*.

The unspecific acting endo- and/or exo-peptidase enzyme is added to the substrate in an effective amount conventionally employed in protein hydrolysis processes, preferably in the range of from about 0.05 to about 15 CPU/100 g of substrate, and more preferably in the range of from about 0.1 to about 5 CPU/100 g of substrate. One CPU (Casein Protease Unit) is defined as the amount of enzyme liberating I micromole of primary amino groups (determined by comparison with a serine standard) per minute from casein under standard conditions, i.e., incubation for 30 minutes at 25° C. and pH 9.5. The analytical method AF 228/1, which is incorporated herein by reference, is available upon request from Novo Nordisk A/S, Bagsvaerd, Denmark.

Each enzymatic treatment may take place at any temperature at which the enzyme preparation does not become inactivated, preferably in the range of from about 20° C. to about 70° C. The enzyme preparation may then be inactivated by increasing the temperature, e.g., to above about 70° C., or by decreasing the pH, e.g., below about 4.0.

The proteinaceous substrate used in the methods of the present invention may consist of intact proteins, prehydrolyzed proteins (i.e., peptides), or a mixture thereof. The proteinaceous substrate may be of vegetable or animal origin. Preferably, the proteinaceous substrate is of vegetable origin, e.g., soy protein, grain protein, e.g., wheat gluten, corn gluten, barley, rye, oat, rice, zein, lupine, cotton seed protein, rape seed protein, peanut, alfalfa protein, pea protein, fabaceous bean protein, sesame seed protein, or sunflower. A proteinaceous substrate of animal origin may be whey protein, casein, meat proteins, fish protein, red blood cells, egg white, gelatin, or lactoalbumin.

The present invention also relates to protein hydrolysates produced by these methods.

Other Uses

The present invention also relates to methods of deactivating enzymes with a polypeptide of the present invention.

Furthermore, a polypeptide of the present invention may be useful for a number of purposes in which a specific cleavage of peptide sequences is desirable. For instance, some proteins or peptides are synthesized in the form of inactive precursors comprising a number of additional amino acid residues at the N-terminal of the mature protein. A polypeptide of the present invention could provide the necessary post-translational processing to activate such precursor proteins.

Compositions

In a still further aspect, the present invention relates to polypeptide compositions comprising a polypeptide of the present invention. Preferably, the compositions are enriched in a polypeptide of the present invention. In the present context, the term "enriched" indicates that the dipeptidyl aminopeptidase activity of the polypeptide composition has been increased, e.g., with an enrichment factor of 1.1.

The polypeptide composition may comprise a polypeptide of the invention as the major enzymatic component, e.g., a mono-component polypeptide composition. Alternatively, the composition may comprise multiple enzymatic activities, such as an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, or a xylanase. The additional enzyme(s) may be producible by means of a microorganism belonging to the genus Aspergillus, preferably *Aspergillus aculeatus, Aspergillus awamori, Aspergillus niger*, or *Aspergillus oryzae*, or Trichoderma, Humicola, preferably *Humicola insolens*, or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum*.

In a preferred embodiment, the invention relates to a flavor-improving composition comprising a polypeptide with dipeptidyl aminopeptidase activity and a carrier. Any suitable carrier known in the art may be used. In another preferred embodiment, the flavor-improving composition further comprises an endopeptidase. In another preferred embodiment, the flavoring composition further comprises one or more unspecific-acting endo- and/or exo-peptidase enzymes. In another preferred embodiment, the flavoring composition further comprises one or more specific-acting endo- and/or exo-peptidase enzymes.

In a preferred embodiment, the specific acting proteolytic enzyme is an endopeptidase such as a glutamyl endopeptidase (EC 3.4.21.19); a lysyl endopeptidase (EC 3.4.21.50); a leucyl endopeptidase (EC 3.4.21.57); a glycyl endopeptidase (EC 3.4.22.25); a prolyl endopeptidase (EC 3.4.21.26); trypsin (EC 3.4.21.4) or a trypsin-like (lysine/arginine specific) endopeptidase; or a peptidyl-Asp metalloendopeptidase (EC 3.4.24.33).

The glutamyl endopeptidase (EC 3.4.21.19) may preferably be obtained from a Bacillus strain, in particular *Bacillus licheniformis* and *Bacillus subtilis*, a Staphylococcus strain, in particular *Staphylococcus aureus*, a Streptomyces strain, in particular *Streptomyces thermovulgaris* and *Streptomyces griseus*, or a Actinomyces strain.

The lysyl endopeptidase (EC 3.4.21.50) may preferably be obtained from a Achromobacter strain, in particular *Achromobacter lyticus*, a Lysobacter strain, in particular *Lysobacter enzymogenes*, or a Pseudomonas strain, in particular *Pseudomonas aeruginosa*.

The leucyl endopeptidase (EC 3.4.21.57) may be of plant origin.

The glycyl endopeptidase (EC 3.4.22.25) may preferably be obtained from the papaya plant (*Carica papaya*).

The prolyl endopeptidase (EC 3.4.21.26) may preferably be obtained from a Flavobacterium strain, or it may be of plant origin.

The trypsin-like endopeptidase may preferably be obtained from a Fusarium strain, in particular *Fusarium oxysporum*, e.g., as described in WO 89/06270 or WO 94/25583.

The peptidyl-Asp metalloendopeptidase (EC 3.4.24.33) may preferably be obtained from a Pseudomonas strain, in particular *Pseudomonas fragi*.

In another preferred embodiment, the specific acting proteolytic enzyme is an exo-peptidase that may act from either end of the peptide.

In a preferred embodiment, the specific acting proteolytic enzyme is an aminopeptidase such as a leucyl aminopeptidase (EC 3.4.11.1); or a tripeptide aminopeptidase (EC 3.4.11.4).

In another preferred embodiment, the specific acting proteolytic enzyme is a carboxypeptidase such as a proline carboxypeptidase (EC 3.4.16.2); a carboxypeptidase A (EC 3.4.17.1); a carboxypeptidase B (EC 3.4.17.2); a carboxypeptidase C (EC 3.4.16.5); a carboxypeptidase D (EC 3.4.16.6); a lysine (arginine) carboxypeptidase (EC 3.4.17.3); a glycine carboxypeptidase (EC 3.4.17.4); an alanine carboxypeptidase (EC 3.4.17.6); a glutamate carboxypeptidase (EC 3.4.17.11); a peptidyl-dipeptidase A (EC 3.4.15.1); or a peptidyl-dipeptidase (EC 3.4.15.5).

The polypeptide compositions may be prepared in accordance with methods known in the art and may be in the form of a liquid or a dry composition. The polypeptide may be stabilized by methods known in the art.

The present invention also relates to food products, e.g., baked products, comprising a protein hydrolysate obtained by the methods of the present invention. Such food products exhibit enhanced organoleptic qualities, such as improvement in flavor, palatability, mouth feel, aroma and crust color.

In the present context, the term "baked products" includes any food prepared from dough, either of a soft or a crisp character. Examples of baked products, whether of a white, light or dark type, which may be advantageously produced by the present invention, are bread, in particular white, whole-meal or rye bread, typically in the form of loaves or rolls; French baguette-type breads; pita breads; tacos; cakes; pancakes; biscuits; crisp breads; and the like.

Such baked products are conventionally prepared from a dough which comprises flour and water, and which is typically leavened. The dough may be leavened in various ways, such as by adding sodium bicarbonate or the like, or by adding a leaven (fermenting dough), but the dough is preferably leavened by adding a suitable yeast culture such as a culture of *Saccharomyces cerevisiae* (baker's yeast). Any of the commercially available *Saccharomyces cerevisiae* strains may be employed.

Further, the dough used in the preparation of the baked products may be fresh or frozen. The preparation of frozen dough is described by K. Kulp and K. Lorenz in "Frozen and Refrigerated Doughs and Batters". A flavor improving composition of the present invention is typically included in the dough in an amount in the range of 0.01–5%, more preferably 0.1–3%.

In the methods of the present invention, a polypeptide of the present invention, an endopeptidase, a transglutaminase, a peptidoglutaminase, one or more specific and/or unspecific acting endo- and/or exo-peptidase enzymes, and/or one or more enzymes specified above may be added, either separately or concurrently, to the mixture from which the dough is made or to any ingredient, e.g., flour, from which the dough is to be made.

The present invention further relates to a pre-mix, e.g., in the form of a flour composition, for dough and/or baked products made from dough, wherein the pre-mix comprises a polypeptide or a flavor-improving composition of the invention and a carrier or baking ingredient, and optionally one or more other enzymes specified above.

In another embodiment, the pre-mix comprises a hydrolysate obtained by the methods of the invention.

The pre-mix may be prepared by mixing the relevant enzymes with a suitable carrier such as flour, starch, a sugar or a salt. The pre-mix may contain other dough-improving and/or bread-improving additives.

In the present context, the term "pre-mix" is a mixture of baking agents, normally including flour, which has been prepared to permit storage under designated conditions and provide convenience in handling during dough preparation processes. Such a pre-mix may be of advantageous use in industrial and commercial bread-baking plants and facilities, as well as in retail bakeries.

The present invention also relates to the use of a hydrolysate produced by the methods of the invention as an additive to food products, such as baked foods, to enhance organoleptic qualities, such as flavor, palatability and aroma.

The hydrolysates enriched in free glutamic acid and/or peptide bound glutamic acid residues obtained by the methods of the present invention may be used in various industrial applications, in particular, where there is a need for the incorporation of functional proteins.

For example, the present invention also relates to food products comprising a hydrolysate enriched in free glutamic acid and/or peptide bound glutamic acid residues obtained by the method of the invention and to animal feed additives comprising a hydrolysate enriched in free glutamic acid and/or peptide bound glutamic acid residues obtained by the methods of the present invention.

The present invention is further described by the following examples which should not be construed as limiting the scope of the invention.

EXAMPLES

Example 1

Purification of FLAVOURZYME™ Dipeptidyl Aminopeptidase I

Dipeptidyl aminopeptidase I was purified from a FLAVOURZYME™ broth (Novo Nordisk A/S, Bagsvaerd, Denmark). The FLAVOURZYME™ broth was produced by cultivation of *Aspergillus oryzae* strain 1568 (ATCC 20386) in a medium comprised of carbon and nitrogen sources and trace metals. First, the broth (20 ml containing 720 mg of protein) was diluted with 180 ml of 20 mM sodium phosphate pH 7.0 buffer and filtered using Nalgene Filterware equipped with a 0.45 µm filter. The filtered solution was loaded onto a 24×130 mm column containing 31 ml of Q-Sepharose, Big Beads (Pharnacia Biotech AB, Uppsala, Sweden) pre-equilibrated with 20 mM sodium phosphate pH 7.0 buffer. The dipeptidyl aminopeptidase I was eluted using 20 mM sodium acetate buffer, pH 3.5. Dipeptidyl aminopeptidase I activity was monitored at 405 nm using 1 mg/ml Ala-Pro-p-nitroanilide as substrate in 50 mM sodium phosphate pH 7.5 buffer. The resultant solution containing dipeptidyl aminopeptidase I activity was concentrated to 38 ml by ultrafiltration with a PM10 membrane (Amicon, New Bedford, Mass.) and then the pH was adjusted to pH 7.0 using a 20 mM $Na_2HPO_4$ solution.

The resultant solution was loaded onto a 24×130 mm column containing 31 ml of Q-Sepharose Big Beads (Pharnacia Biotech AB, Uppsala, Sweden) pre-equilibrated with 20 mM sodium phosphate pH 7.0 buffer. The dipeptidyl aminopeptidase I was eluted with a 0 to 0.3 M NaCl gradient in 20 mM sodium phosphate pH 7.0 buffer. Fractions were monitored for dipeptidyl aminopeptidase I activity as described above. The fractions containing dipeptidyl aminopeptidase I activity were collected, pooled, desalted and concentrated using ultrafiltration against 20 mM sodium phosphate pH 7.0 buffer.

The resultant solution was loaded onto a MonoQ 16/10 (20 ml) pre-packed column (Pharmacia Biotech AB, Uppsala, Sweden) pre-equilibrated with 20 mM sodium phosphate pH 7.0 buffer. The dipeptidyl aminopeptidase I was eluted with a 0 to 0.27 M NaCl gradient in 20 mM sodium phosphate pH 7.0 buffer. Fractions were monitored for dipeptidyl aminopeptidase I activity as described above. The fractions between 0.200 and 0.212 M NaCl were collected, pooled, and rebuffered with 1.7 M $(NH_4)_2SO_4$/20 mM sodium phosphate pH 7.0 buffer using ultrafiltration as described above.

The resultant solution was loaded onto a 7×50 mm column containing Phenyl Superose resin (Pharmacia Biotech AB, Uppsala, Sweden) pre-equilibrated with 1.7 M $(NH_4)_2SO_4$/20 mM sodium phosphate pH 7.0 buffer solution. The dipeptidyl aminopeptidase I was eluted with a reverse 1.7 to 0 M $(NH_4)_2SO_4$ gradient in 20 MM sodium phosphate pH 7.0 buffer. Fractions were monitored for dipeptidyl aminopeptidase I activity as described above. Two fractions possessing highest activity toward Ala-Pro-p-nitroanilide were found to be at least 95% homogeneous based on SDS-PAGE analysis. The major band had a molecular weight of approximately 95 kDa (range of 93–96 kDa).

Example 2

Protein Sequencing and Amino Acid Analysis Methods

N-terminal sequencing of the partially purified dipeptidyl aminopeptidase I described in Example 1 and a digested fragment of the dipeptidyl aminopeptidase I was performed on an Applied Biosystems 476A Protein Sequencer (Perkin Elmer/Applied Biosystems Division, Foster City, Calif.) with on-line HPLC and liquid phase trifluoroacetic acid (TFA) delivery. Samples of the purified dipeptidyl aminopeptidase I were transblotted onto Novex PVDF membranes (Novex, San Diego, Calif.) from SDS-PAGE gels and sequenced from a blott cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 15 ml of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis software.

The partially purified dipeptidyl aminopeptidase I (MonoQ peak of Example 1) was also subjected to in-gel digestion with trypsin to generate peptide fragments of the enzyme for protein sequencing. The trypsin-digested dipeptidyl aminopeptidase I was separated by SDS-PAGE electrophoresis using 8–16% Novex Tris-glycine gels (Novex, San Diego, Calif.). Eight Coommassie blue stained gel pieces corresponding to a molecular weight of 95 kDa were excised and washed extensively with 200 mM $NH_4HCO_3$ in 50% acetonitrile. The gel pieces were subsequently reduced in 1 mM dithiothreitol (DTT) at 37° C. for 20 minutes and alkylated with an equal volume of 100 mM iodoacetic acid at room temperature for 20 minutes in the dark. Gel pieces were washed repeatedly with 200 mM $NH_4HCO_3$ in 50% acetonitrile. Supernatants were removed and gel pieces were dried on a Speed-Vac (Savant Instruments, Farmingdale, N.Y.). The gel pieces were rehydrated in a solution containing 0.033 mg of sequencing grade modified porcine trypsin (Promega, Madison, Wis.) per ml of 135 mM $NH_4HCO_3$. The solution was prepared by diluting 1 part of 0.1 mg of the trypsin per ml of trypsin resuspension buffer (Promega, Madison, Wis.) into 2 parts of 200 mM $NH_4HCO_3$. The gel pieces were incubated at 37° C. for 20 hours. The peptide fragments were extracted from the gel in repetitive washes of 0.1% TFA in 60% acetonitrile for 1 hour each. The extracted peptides were dried and reconstituted in 0.05% TFA in 25% acetonitrile and then further diluted into 0.05% TFA. The peptide fragments were filtered using a Micropure 0.45 µm filter unit (Amicon, Inc., Beverly, Mass.). The peptide fragments were then separated by reverse-phase HPLC using a Hewlett-Packard 1090L HPLC equipped with a 2.1×250 mm Vydac C 18-RP column (5 micron). A step gradient was used with 0.1% TFA in 80% acetonitrile as the eluant. The peptide samples were hand collected and then subjected to N-terminal sequencing.

The partially purified dipeptidyl aminopeptidase I was also subjected to cyanogen bromide to generate peptide fragments of the enzyme for sequencing. The dipeptidyl aminopeptidase I was digested with cyanogen bromide by reconstituting a dried sample of the partially purified n 70% formic acid with a few crystals of cyanogen bromide and incubating for 18 hours at room temperature in the dark. The peptide fragments were separated by SDS-PAGE electrophoresis using 10–20% Novex Tricine gels (Novex, San Diego, Calif.) and sequenced as described above.

N-terminal sequencing of the dipeptidyl aminopeptidase I revealed that the N-terminus was apparently blocked. A weak sequence was obtained as follows where amino acid residues in parentheses are not 100% certain and residues marked with an X could not be determined:

Peptide 1: XEGSKRLTFXETVVKQAIT(P) (SEQ ID NO:3)

The cyanogen bromide-degraded fragments had the following amino acid sequences where amino acid residues underlined matched 100% with a dipeptidyl aminopeptidase I of *Saccharomyces cerevisiae* (Anna-Arriola and Herskowitz, 1994, *Yeast* 10: 801–810; Galisson and Dujon, 1996, *Yeast* 12: 877–885):

Peptide 2: QRLPPGFSPDKKYPILFTPYGG (SEQ ID NO:4)

Peptide 3: KYIGPIK (SEQ ID NO:5)

Peptide 4: GEGSKRL (SEQ ID NO:6)

In-gel digestion with trypsin produced the following peptides where amino acid residues underlined matched 100% with the deduced amino acid sequence of the *Aspergillus oryzae* dipeptidyl aminopeptidase I nucleic acid sequence described in Example 7:

Peptide 5: XPILFTPY (SEQ ID NO:7)

Peptide 6: XVPLMPDQ(Q)GDIOYAQ (SEQ ID NO:8)

Example 3

Genomic DNA Extraction

*Aspergillus oryzae* 1568 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg/ml and the mixture was then incubated at 37° C. for 30 minutes Proteinase K (200 μg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

Example 4

PCR Amplification of *Aspergillus Oryzae* 1568 Dipeptidyl Aminopeptidase I

The forward degenerate oligonucleotide primer was designed to the peptide sequence DW(I/V)YEEE, a conserved motif found in most published dipeptidyl aminopeptidase I protein sequences. The reverse degenerate oligonucleotide primer was designed to a partial peptide, PPGFSDKKYP, of peptide 2 (SEQ ID NO:4) as described in Example 2. The degenerate oligonucleotide primers shown below were synthesized with an Applied Biosystems Model 394 DNA/RNA Synthesizer, according to the manufacturer's instructions, for use to PCR amplify dipeptidyl aminopeptidase I gene fragments from *Aspergillus oryzae* 1568 genomic DNA:

Forward primer: 5'-GAYTGGITITAYGARGARGAR-3' (SEQ ID NO:9) Reverse primer: 5'-GGRTAYTTYTTRTCIGGISWRAAICCIGGIGG-3' (SEQ ID NO:10)

(R=A or G, Y=C or T, S=G or C, W=A or T, I=Inosine)

Amplification reactions (100 μl) were prepared using approximately 1 μg of genomic DNA isolated from an *Aspergillus oryzae* 1568 as described in Example 3 as the template. Each reaction contained the following components: 1 μg genomic DNA, 40 pmol forward primer, 40 pmol reverse primer, 200 μM each of dATP, dCTP, dGTP, and dTTP, 1×Taq polymerase buffer (Perkin-Elmer Corp., Branchburg, N.J.), and 2.5 Units of Taq polymerase (Perkin-Elmer Corp., Branchburg, N.J.). The reactions were incubated in a Perkin-Elmer Model 480 Thermal Cycler programmed as follows: Cycle 1 at 94° C. for 2 minutes, 45° C. for one minutes, and 72° C. for one minute; and cycles 2–30 each at 94° C. for one minute, 45° C. for one minute, and 72° C. for one minute. The reaction products were isolated on a 1% agarose gel (Eastman Kodak, Rochester, N.Y.). An approximately 1.0 kb product band was excised from the gel and purified using GenElute spin columns (Supelco, Bellefonte, Pa.) according to the manufacturer's instructions. The purified PCR product was subsequently cloned into a pCRII vector (Invitrogen, San Diego, Calif.) and the DNA sequence was determined using lac forward and reverse primers (New England BioLabs, Beverly, Mass.).

A dipeptidyl aminopeptidase I gene segment consisting of approximately 321 codons (963bp) was amplified from *Aspergillus oryzae* 1568 with the dipeptidyl aminopeptidase I PCR primers described above. DNA sequence analysis shows that the amplified gene segment encoded a portion of the corresponding *Aspergillus oryzae* 1568 dipeptidyl aminopeptidase I gene. The dipeptidyl aminopeptidase I gene segment was used to probe an *Aspergillus oryzae* 1568 genomic DNA library.

Example 5

Construction of DNA Libraries

A genomic DNA library was constructed in the bacteriophage cloning vector λZipLox (Life Technologies, Gaithersburg, Md.). First, total cellular DNA was partially digested with Tsp509I and size-fractionated on 1% agarose gels. DNA fragments migrating in the size range 3–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *Escherichia coli* Y1090ZL cells (Life Technologies, Gaithersburg, Md.). The unamplified genomic DNA library contained $3.1 \times 10^6$ pfu/ml (background titers with no DNA were $2.0 \times 10^4$ pfu/ml).

Example 6

Identification of Dipeptidyl Aminopeptidase I Clones

Approximately 10,000 plaques from the library described in Example 5 were screened by plaque-hybridization using the dipeptidyl aminopeptidase I PCR fragment from *Aspergillus oryzae* 1568 as the probe. The DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 μg/ml of denatured and sheared herring sperm DNA. The dipeptidyl aminopeptidase I gene fragment isolated from the *Aspergillus oryzae* 1568 genomic DNA as described in Example 2 was radiolabeled using the Random Primed DNA Labeling Kit (Boehringer Mannheim, Mannheim, Germany), denatured by adding NaOH to a final concentration of 0.1 M, and added to the hybridization solution at an activity of approximately $1 \times 10^6$ cpm per ml of hybridization solution. The mixture was incubated overnight at 45° C. in a shaking water bath. Following incubation, the membranes were washed once in 2×SSC with 0.2% SDS at 55° C. followed by two washes in 2×SSC at the same temperature. The membranes were dried on blotting paper for 15 minutes, wrapped in SaranWrap™, and exposed to X-ray film overnight at −70° C. with intensifying screens (Kodak, Rochester, N.Y.).

Based on the production of strong hybridization signals with the probe, three plaques, designated E. coli DH5α MWR52A, E. coli DH5α MWR52B, and E. coli DH5α MWR52C were chosen for further study. The three plaques were purified twice in E. coli Y1090ZL cells and the dipeptidyl aminopeptidase I genes were subsequently excised from the λZipLox vector as pZL1-derivatives (D'Alessio et al., 1992, Focus® 14:76) using in vivo excision by infection of E. coli DH10BZL cells (Life Technologies, Gaithersburg, Md.). The three plasmid containing colonies were inoculated into three ml of LB plus 50 μg/ml carbenicillin medium and grown overnight at 37° C. Miniprep DNA was prepared from each of these cultures using the Wizard 373 DNA Purification Kit (Promega, Madison, Wis.). The dipeptidyl aminopeptidase I encoding plasmid (pMWR52) was confirmed by DNA sequencing.

Example 7

DNA Sequence Analysis of Aspergillus oryzae 1568 Dipeptidyl Aminopeptidase I Gene DNA sequencing of the dipeptidyl aminopeptidase I gene contained on pMWR52 in E. coli DH5α MWR52 described in Example 6 was performed with an Applied Biosystems Model 377 Automated DNA Sequencer (Applied Biosystems, Inc., Foster City, Calif.) on both strands using the primer walking technique with dye-terminator chemistry (Giesecke et al., 1992, Journal of Virology Methods 38: 47–60). Oligonucleotide sequencing primers were designed to complementary sequences in the dipeptidyl aminopeptidase I gene and were synthesized on an Applied Biosystems Model 394 DNA/RNA Synthesizer according to the manufacturer's instructions.

The nucleotide sequence of the gene encoding the Aspergillus oryzae 1568 dipeptidyl aminopeptidase I is shown in FIG. 1 (SEQ ID NO:1). Sequence analysis of the cloned insert revealed an open reading frame of 2396 nucleotides (excluding the stop codon) interrupted by an 83 bp intron. The G+C content of this open reading frame was 55.3%. The deduced amino acid sequence encoded a protein of 771 amino acids (SEQ ID NO:2). Based on the rules of van Heijne (van Heijne, 1984, Journal of Molecular Biology 173: 243–251), the first 16 amino acids likely comprise a secretory signal peptide which directs the nascent polypeptide into the endoplasmic reticulum (boxed in FIG. 1).

The amino acid sequences of the partial peptides derived from the purified dipeptidyl aminopeptidase I as described in Example 2 are underlined in FIG. 1 and are consistent with those found in the deduced amino acid sequence (SEQ ID NO:2) of the Aspergillus oryzae 1568 dipeptidyl aminopeptidase I cDNA.

Using the Clustal alignment program (Higgins, 1989, CABIOS 5: 151–153) to compare the deduced amino acid sequence of the Aspergillus oryzae 1568 dipeptidyl aminopeptidase I to that of a Saccharomyces cerevisiae dipeptidyl aminopeptidase I (Anna-Arriola and Herskowitz, 1994, Yeast 10: 801–810) (SEQ ID NO:11), a 23.2% identity was observed.

Example 8

Construction of a Aspergillus oryzae 1568 Dipeptidyl Aminopeptidase Fusarium Expression Vector The coding region of Aspergillus oryzae dipeptidyl aminopeptidase I was amplified and the resulting fragment was cloned into pDM181 for expression in Fusarium. pDM181 provides the Fusarium trypsin (SP387) promoter and terminator, and the bar selectable marker gene. Specifically, the fragment was amplified by PCR using a sense primer (P1) designed to the first in-frame ATG and extending 13 bp downstream and an antisense primer (P2) designed to a region of the transcriptional stop codon and extending 10 bp downstream. To facilitate the cloning of the amplified fragment the sense and antisense primers contain a SwaI and a PacI restriction site, respectively. The oligonucleotide primers shown below were synthesized using an ABI Model 394 DNA/RNA Synthesizer (Applied Biosystems, Inc., Foster City, Calif.) according to the manufacturer's instructions.

SwaI

P1: 5'-GATTTAAATCACCATGAAGGTACGTCAATT CCACTG-3' (SEQ ID NO:12)

PacI

P2: 5'-GTTAATTAATCTACTCCTCCAAGTCCTTCTT AGTCC-3' (SEQ ID NO:13)

The 50 μl PCR solution (10 mM Tris-HCl pH 8.3, 50 mM KCl, 1.5 mM $MgCl_2$, 0.01% w/v gelatin) contained approximately 200 ng of pMWR52 DNA, 200 μM each of dATP, dCTP, dGTP, and dTTP, and 50 pmol of each PCR primer described above. Five units of PWO polymerase (Boehringer Mannheim, Indianapolis, Ind.) were added and the reaction was incubated at 95° C. for 3 minutes and cooled to 80° C. The reaction was then cycled 30 times, each cycle at 95° C. for 30 seconds, 57° C. for 1 minute, and 72° C. for 1 m Perkin-Elmer 9600 Thermal Cycler. Following the last cycle, the reaction incubated for 5 minutes at 72° C.

A predicted 2.4 kb fragment was isolated by digestion with SwaI and PacI and was cloned into pDM181 (FIG. 2) digested with the same restriction endonucleases to create pMWR54 (FIG. 3). To verify the fidelity of the cloned PCR fragment, the fragment was sequenced according to the method of Hattori and Sakaki (1986, Analytical Biochemistry 152: 232–237) using an automated Applied Biosystems Model 373A Sequencer (Applied Biosystems, Inc., Foster City, Calif.) according to the manufacturer's instructions.

Sequencing of the cloned dipeptidyl aminopeptidase amplified insert of pMWR54 confirmed that there were no differences in the sequence described in SEQ ID NO:1.

Example 9

Transformation of Fusarium CC1–3 and Analysis of Transformants

Fusarium strain CC1–3, a highly branched morphological mutant of Fusarium strain A3/5 (ATCC 20334) (Wiebe et al., 1992, Mycological Research 96: 555–562; Wiebe et al., 1991, Mycological Research 95: 1284–1288; Wiebe et al., 1991, Mycological Research 96: 555–562), was grown in a liquid medium containing Vogel's salts, (Vogel, 1964, Am. Nature 98: 435–446), 25 mM $NaNO_3$, and 1.5% glucose for 4 days at 28° C. and 150 rpm. Conidia were purified by filtration through 4 layers of cheesecloth and finally through one layer of Miracloth. Conidial suspensions were concentrated by centrifugation. Fifty ml of YPG medium comprised of 1% yeast extract, 2% bactopeptone, and 2% glucose were inoculated with approximately 108 conidia, and incubated for 14 hours at 24° C. and 150 rpm. Resulting hyphae were trapped on a sterile 0.4 mm filter and washed successively with sterile distilled water and 1.0 M $MgSO_4$. The hyphae were resuspended in 10 ml of NOVOZYM 234™ solution (2–10 mg/ml in 1.0 M MgSO$_4$) and digested for 15–30 minutes at 34° C. with agitati 80 rpm. Undigested hyphal material was removed from the resulting protoplast suspension by successive filtration through 4 layers of cheesecloth and through Miracloth. Twenty ml of 1 M sorbitol were combined with the protoplast solution. After mixing, the protoplasts were pelleted by centrifugation and washed successively by resuspension and centrifugation in 20 ml of 1 M sorbitol and in 20 ml of STC (0.8 M sorbitol, 0.05 M Tris pH 8.0, 0.05 M CaCl$_2$). The washed protoplasts were resuspended in 4 parts STC and 1 part SPTC (0.8 M sorbitol, 40% PEG 4000, 0.05 M Tris pH 8.0, 0.05 M CaCl$_2$) at a concentration of 5×10$^7$/ml.

One hundred ml of protoplast suspension were added to 10 µg of pMWR54 in polypropylene tubes (17×100 mm), mixed and incubated on ice for 30 minutes. One ml of SPTC was mixed gently into the protoplast suspension and incubation was continued at room temperature for 20 minutes. 12.5 ml of molten solution (cooled to 40° C.) consisting of 1X Vogel's salts, 25 mM NaNO$_3$, 0.8 M sucrose and 1% low melting agarose (Sigma Chemical Company, St. Louis, Mo.) were mixed with the protoplasts and then plated onto an empty 100 mm Petri plate. Incubation was continued at room temperature for 10 to 14 days. After incubation at room temperature for 24 hours, 12.5 ml of the identical medium plus 10 mg of BASTA™ (Hoechst Schering, Rodovre, Denmark) per ml were overlayed onto the Petri plate. BASTA™ was extracted twice with phenol:chloroform:isoamyl alcohol (25:24:1), and once with chloroform:isoamyl alcohol (24:1) before use.

After two weeks, 21 transformants were apparent. A mycelial fragment from the edge of each transformant was transferred to individual wells of a 24 well plate containing Vogel's/BASTA™ medium. The medium was composed per liter of 25 g of sucrose, 25 g of Noble agar, 20 ml of 50X Vogel's salts (Vogel, 1964, supra), 25 mM NaNO$_3$, and 10 g of BASTA™. The plate was sealed in a plastic bag to maintain moisture and incubated approximately one week at room temperature.

Example 10

Expression of *Aspergillus Oryzae* 1568 Dipeptidyl Aminopeptidase I in Fusarium

A mycelial fragment from each of the 21 Fusarium CC1–3 transformants described in Example 9 was inoculated into 20 ml of M400Da medium composed per liter of 50 g of maltodextrin, 2.0 g of MgSO$_4$-7H$_2$O, 2.0 g of KH$_2$PO$_4$, 4.0 g of citric acid, 8.0 g of yeast extract, 2.0 g of urea, and 0.5 ml of trace metals solution and incubated for 5 days at 30° C. and 200 rpm. The medium was adjusted to pH 6.0 with 5 N NaOH. The trace metals solution was compsoed per liter of 14.3 g of ZnSO$_4$-7H$_2$O, 2.5 g of CuSO$_4$-5H$_2$0, 0.5 g of NiCl$_2$O, 13.8 g of FeSO$_4$-7H$_2$O, 8.5 g of MnSO$_4$-H$_2$O, and 3.0 g of citric acid. The untransformed host was also run as a control. One ml of each culture supernatant was harvested at 5 days and stored at 4° C. Dipeptidyl aminopeptidase I activity was determined by mixing 1 µl of the enzyme supernatant with 200 µl of a Ala-Pro-pNA substrate stock solution containing 2 mg of Ala-Pro-pNA per ml of 50 mM sodium phosphate pH 7.5 and monitoring the change in absorbance at 405 nm and ambient temperature.

Culture supernatants from 19 of the 21 primary transformants of pMWR54 were positive when assayed for dipeptidyl aminopeptidase I activity.

The Fusarium primary transformants #1 and #16 were cultivated in 125 ml shake flasks for 5 days at 30° C. in 25 ml of M400Da medium. The whole culture broths from the Fusarium primary transformants were filtered using a double layer of Miracloth. The filtrate was recovered and then frozen at −20° C.

Example 11

Purification of Recombinant *Aspergillus oryzae* 1568 Dipeptidyl Aminopeptidase I Produced in Fusarium The recombinant dipeptidyl aminopeptidase I was purified from the Fusarium broth of primary transformant #1 described in Example 10. The broth (20 ml) was filtered through Nalgene filterware equipped with a 0.45 micron filter (Nalgene, Rochester, N.Y.). The sample was diluted 10-fold using 20 mM sodium phosphate pH 7.0 buffer and concentrated using a ultrafiltration system (Amicon, Beverly, Mass.) utilizing a PM10 ultrafiltration membrane. The conductivity of the sample was 2.5 mS.

The sample was then loaded onto a column (XK-26) containing 60 ml of Q-Sepharose Big Beads, which had been pre-equilibrated with 400 ml of 20 mM sodium phosphate pH 7.0 buffer. The column was washed until baseline was reached. At a flow rate of 5 ml/min, the dipeptidyl aminopeptidase I was eluted with a linear gradient from 0–0.40 M NaCl in 20 mM sodium phosphate buffer pH 7.0 buffer over 10 column volumes. The dipeptidyl aminopeptidase I eluted at ~0.24 M NaCl. SDS-PAGE was performed on the fractions active Ala-Pro-pNA. The substrate was prepared by dissolving 2 mg of Ala-Pro-pNA (Bachem, Torrance, Calif.) in 20 µl of DMSO. Then, 980 µl of 50 mM sodium phosphate pH 7.5 buffer was added. In a 96 well microtiter plate, 100 µl of the substrate solution was added to 100 µl of *Aspergillus oryzae* dipeptidyl aminopeptidase I (100 fold diluted in 50 mM sodium phosphate buffer pH 7.5) and the increase in absorbance at 405 nm was measured for 4 minutes using a SpectroMax 340 plate reader (Molecular Devices, Sunnyvale, Calif.). The homogeneous fractions were then pooled.

Example 12

Characterization of Recombinant *Aspergillus oryzae* 1568 Dipeptidyl Aminopeptidase I The purified dipeptidyl aminopeptidase I described in Example 11 was characterized with respect to pH optimum, temperature stability, substrate specificity, and kinetic parameters.

The pH optimum was determined using Ala-Pro-pNA (HCI salt) as substrate in the universal buffer composed of 0.125 M citric acid, 0.125 M mono basic sodium phosphate, and 0.125 M boric acid pH was adjusted to 4.35–9.83 with 10 N NaOH, in 0.5 pH increments. The Ala-Pro-pNA substrate was prepared by dissolving 100 mg of Ala-Pro-pNA in 1 ml of DMSO and adding 20 µl of the Ala-Pro-pNA-DMSO solution to 980 µl of the universal buffer at the various pH values at ambient temperature. The assay was initiated by adding a 10 µl aliquot of the dipeptidyl aminopeptidase I diluted 20-fold in water to 200 µl of 2 mg/ml Ala-Pro-pNA at the various pH values. The absorbance at 405 nm was monitored for 5 minutes. Autohydrolysis of the substrate as a control was determined by adding 10 µl of water to 200 µl of 2 mg/ml Ala-Pro-pNA at the various pH values.

The results shown in Table I below demonstrated that the dipeptidyl aminopeptidase I possessed activity toward Ala- Pro-pNA as substrate over the measured pH range 4.35 to 9.83 with optimal activity at pH ~8.7. Autohydrolysis of the substrate was observed at pH values greater than 7.

TABLE 1

| pH | Average Activty | Average Background | Avg. Activity-Background | Relative Activty |
|---|---|---|---|---|
| 4.35 | 8.75 mOD/min | 0 mOD/min | 8.75 mOD/min | 0.023 |
| 4.87 | 32.5 | 0 | 32.5 | 0.088 |
| 5.36 | 75.75 | 0 | 75.75 | 0.20 |
| 5.86 | 113.8 | 0 | 113.8 | 0.307 |
| 6.38 | 135.48 | 0 | 135.48 | 0.365 |
| 6.85 | 168.45 | 2 | 166.45 | 0.45 |
| 7.2 | 188.86 | 2 | 186.86 | 0.503 |
| 7.51 | 230.97 | 3 | 227.97 | 0.615 |
| 7.97 | 308.52 | 5.8 | 302.72 | 0.817 |
| 8.71 | 383.15 | 12.5 | 370.65 | 1 |
| 9.32 | 247.68 | 29.8 | 217.88 | 0.588 |
| 9.83 | 171 | 74 | 97 | 0.261 |

The temperature stability of the dipeptidyl aminopeptidase I was determined using the following protocol: 490 µl of 50 mM sodium phosphate buffer pH 7.5 was preincubated at 37°, 45°, 55°, 60°, 65°, 70°, and 75° C. for 30 minutes in a 1.7 ml Eppendorf tube. Then 10 µl of purified dipeptidyl aminopeptidase I was added and the sample was then incubated for an additional 20 minutes. The samples were then placed on ice. Once the incubations were completed for all the temperatures, the samples were then assayed for activity using Ala-Pro-pNA as substrate.

The assay was performed by mixing 30 µl of the incubation mixtures for the various temperatures with 200 µl of 2 mg/ml Ala-Pro-pNA in 50 mM sodium phosphate pH 7.5 buffer) at ambient temperature. The absorbance at 405 nm was monitored for 5 minutes.

The results shown in Table 2 demonstrated that the dipeptidyl aminopeptidase I retained 90% of its activity after a 20 minute incubation at 65° C., pH 7.5.

TABLE 2

| Temperature (° C.) | Percent activity relative to 37° C. |
|---|---|
| 37 | 100 |
| 45 | 103 |
| 55 | 103 |
| 65 | 92.5 |
| 70 | 37.7 |
| 75 | 0.7 |

The relative activity of various mono-, di-, and tri-peptide para-nitroanilide substrates were assayed relative to Ala-Pro-pNA with the purified dipeptidyl aminopeptidase I diluted 100-fold in 50 mM sodium phosphate pH 7.5 buffer. Each substrate was dissolved in DMSO to a concentration of 100 mg/ml and then diluted 50 fold in 50 mM sodium phosphate pH 7.5 buffer to 2 mg/ml. The assay was performed by mixing 100 µl of the substrate solution with 100 µl of the dipeptidyl aminopeptidase I solution and monitoring the change in absorbance at 405 nm and ambient temperature.

The results shown in Table 3 demonstrated that the dipeptidyl aminopeptidase I preferably hydrolyzed Xaa-Pro-pNA and Xaa-Ala-pNA substrates where Xaa corresponds to any natural amino acid.

TABLE 3

| Substrate: | Activity (mOD/min) | Percent Activity Relative to Ala-Pro-pNA |
|---|---|---|
| Gly-Arg-pNA | 0 | 0 |
| Gly-Pro-pNA | 125 | 51.25 |
| Arg-Pro-pNA | 103 | 42.17 |
| Val-Ala-pNA | 49.5 | 20.3 |
| Gly-Glu-pNA | <2 | 0 |
| Ala-Pro-pNA | 244 | 100 |
| Ala-Ala-pNA | 30.2 | 12.4 |
| Asp-Pro-pNA | 70.95 | 29 |
| Leu-pNA | 0 | 0 |
| Ala-pNA | 0 | 0 |
| Ala-Ala-Pro-pNA | 10.6 | 4.3 |

The kinetic parameters for various dipeptidyl aminopeptidase I substrates was determined using the following protocol. The substrates included Ala-Pro-pNA, Asp-Pro-pNA, and Ala-Ala-pNA. Purified dipeptidyl aminopeptidase I with an $A_{280}$ of 1.521 was diluted 25-fold for Ala-Pro-pNA, 20-fold for Asp-Pro-pNA, and 10-fold for Ala-Ala-pNA in water. Each substrate was dissolved in DMSO to a concentration of 100 mg/ml and then diluted 50 fold in 50 mM sodium phosphate pH 7.5 buffer to 2 mg/ml. In a 96 well microtiter plate, 10 µl of purified dipeptidyl aminopeptidase I was incubated with each substrate as follows except the 200 µl substrate assay was not performed with the Asp-Pro-pNA substrate, and the absorbance at 405 nm was measured for 3 minutes:

1. 200 µl of 2 mg/ml substrate+0 µl of 50 mM sodium phosphate buffer pH 7.5
2. 100 µl of 2 mg/ml substrate+100 µl of 50 mM sodium phosphate buffer pH 7.5
3. 50 µl of 2 mg/ml substrate+150 µl of 50 mM sodium phosphate buffer pH 7.5
4. 25 µl of 2 mg/ml substrate+175 µl of 50 mM sodium phosphate buffer pH 7.5
5. 10 µl of 2 mg/ml substrate+190 µl of 50 mM sodium phosphate buffer pH 7.5
6. 5 µl of 2 mg/ml substrate+195 µl of 50 mM sodium phosphate buffer pH 7.5

A Lineweaver-Burke plot was constructed to determine the $K_m$ and the $k_{cat}$ for each substrate, using an average molecular weight of 97 kDa for the differentially glycosylated forms.

For Ala-Pro-pNA, the $K_m$ and $k_{cat}$ were determined to be 0.140 mM and 576.3 min$^{-1}$, respectively.

For Asp-Pro-pNA, the $K_m$ and $k_{cat}$ were determined to be 0.632 mM and 244.3 min$^{-1}$, respectively.

For Ala-Ala-pNA, the $K_m$ and $k_{cat}$ were determined to be 1.08 mM and 106.5 min$^{-1}$, respectively.

Example 13

Purification of *Aspergillus oryzae* 1568 Aminopeptidase I

A 50 ml volume of FLAVOURZYME™ preparation described in Example 1 was centrifuged at 10,000 rpm for 10 minutes. The supernatant was filtered with a 0.2 µm Nalgene filter and the filtrate was then diluted to 350 ml with 20 mM sodium phosphate pH 7.5 buffer. The diluted filtrate was concentrated with an Amicon ultrafiltration cell equipped with a PM10 membrane. More 20 mM phosphate pH 7.5 buffer was added and concentrated 3 more times to adjust the sample to the proper pH and conductivity.

The enzyme solution was then loaded onto a XK-26 column containing Q-Sepharose Big Beads pre-equilibrated with 20 mM phosphate buffer pH 7.5 buffer. A gradient was run from 0 to 300 mM NaCl, and then washed with 350 ml of 300 mM NaCl. Fractions were assayed for Leu-pNA activity according to the following protocol. The substrate was prepared by dissolving 2 mg of Leu-pNA (Sigma Chemical Co., St. Louis, Mo.) in 20 μl of DMSO.

Then, 980 μl of 50 mM sodium phosphate pH 7.5 buffer was added. In a 96 well microtiter plate, 100 μl of the substrate solution was added to 100 μl of *Aspergillus oryzae* aminopeptidase I (100 fold diluted in 50 mM sodium phosphate pH 7.5 buffer) and the increase in absorbance at 405 nm was measured for 4 minutes using a SpectroMax 340 plate reader. The most active fractions were pooled and concentrated as above using PM10 ultrafiltration.

The concentrated sample was diluted to 250 ml with 20 mM phosphate pH 7.5 buffer and loaded onto a Mono-Q 16/10 column (Pharmacia Biotech AB, Uppsala, Sweden). A gradient was run from 0 to 400 mM NaCl. Fractions were assayed for Leu-pNA activity as above. The most active and pure fractions (by SDS-PAGE) were pooled and concentrated as above using using PM10 ultrafiltration.

The sample was diluted in 50 mM phosphate pH 7.0 buffer with 1.7 M ammonium sulfate and concentrated as above. This step was repeated three times. The sample was loaded onto Phenyl Sepharose column (Pharmacia Biotech AB, Uppsala, Sweden) pre-equilibrated with 50 mM sodium phosphate pH 7.0 buffer containing 1.7 M ammonium sulfate. A gradient was run from 1.7 M to 0 M ammonium sulfate, and then washed with 50 mM sodium phosphate pH 7.0 buffer. Fractions were assayed for Leu-pNA activity and purity was checked by SDS-PAGE. Two small bands near 70 kDa were still present.

A 1 ml volume of the most pure fraction was concentrated with a Microcon 10 microconcentrator (Amicon, New Bedford, Mass.). A 100 μl volume of the concentrate was loaded onto a Superose 12 column (Pharmacia Biotech AB, Uppsala, Sweden) pre-equilibrated with 20 mM phosphate buffer pH 7.0 buffer, and eluted in 30 ml of the same buffer. Only one peak was observed. SDS-PAGE analysis revealed two small bands near 70 kDa. These bands were probably an aggregation of the dipeptidyl aminopeptidase, and no further purification was necessary.

All active fractions from the Phenyl Sepharose column were pooled, concentrated, and desalted using PM10 ultrafiltration and 20 mM phosphate pH 7.0 buffer.

Example 14

Synergism between *Aspergillus oryzae* 1568 aminopeptidase I and *Aspergillus oryzae* 1568 Dipeptidyl Aminopeptidase I The substrate was prepared by dissolving 2 mg of Ala-Phe-Pro-pNA (Bachem, Torrance, Calif.) in 20 μl of DMSO. Then, 980 μl of 50 mM sodium phosphate buffer pH 7.5 and 100 μl of ethanol were added. In a 96 well microtiter plate, 100 l of the Ala-Phe-Pro-pNA solution was added to 100 μl of 100-fold diluted aminopeptidase I (Example 12); 100 μl of the Ala-Phe-Pro-pNA solution was added to 100 μl of 100-fold diluted dipeptidyl aminopeptidase I (Example 11); and 100 μl of the Ala-Phe-Pro-pNA solution was added to a mixture of 50 μl of 100-fold diluted aminopeptidase I and 50 μl of 100-fold diluted dipeptidyl aminopeptidase I. The absorbance at 405 nm was measured for 10 minutes.

The purified aminopeptidase I was determined to have an activity of 26.822 LAPUs/ml for Leu-pNA using an extinction coefficient of 10,000 for para-nitroaniline at 405 nm. LAPU is defined as the leucine aminopeptidase activity which is determined as described in AF 298/1-GB (available on request from Novo Nordisk A/S, Denmark). The purified dipeptidyl aminopeptidase I was determined to have an activity of 11.54 DPAPU/ml for Ala-Pro-pNA, also using an extinction coefficient of 10000 for paranitroaniline. At a 100-fold dilution, aminopeptidase I exhibited less than a 2 mOD/min velocity on Ala-Pro-pNA and dipeptidyl aminopeptidase I exhibited less than a 2 mOD/min velocity on Leu-pNA. One hundred-fold diluted aminopeptidase I exhibited no activity on Ala-Phe-Pro-pNA over 10 minutes. One hundred-fold diluted dipeptidyl aminopeptidase I exhibited no activity on Ala-Phe-Pro-pNA over 10 minutes. When a mixture of 100-fold diluted dipeptidyl aminopeptidase I and 100-fold diluted aminopeptidase I were assayed with Ala-Phe-Pro-pNA, a velocity of 122 mOD/min was observed over 10 minutes.

Example 15

Preparation of Protein Hydrolysates with *Aspergillus oryzae* 1568 Dipeptidyl Aminopeptidase I The purified dipeptidyl aminopeptidase I described in Example 11 was tested in degree of hydrolysis assays using geletin, soy, gluten, and casein as substrates according to the following procedure.

The degree of hydrolysis (DH) assays were performed at 50° C. for 18 hours as a mini-hydrolysis on a 10 ml scale using gelatin, soy bean meal tablets, wheat gluten, and sodium-caseinate at a 2% concentration adjusted to pH 7, if necessary, with no pH adjustment during hydrolysis. The hydrolyses were inactivated at 85° C. for 3 minutes in a waterbath. The enzymes used were FLAVOURZYME™ with ALCALASE™ 2.4L (Novo Nordisk A/S, Bagsvrd, Denmark) and dipeptidyl aminopeptidase I with FLAVOURZYME™ and ALCALASE™ 2.4L. FLAVOURZYME™, ALCALASE™, and dipeptidyl aminopeptidase I were dosed at 3 mg, 3 mg, 0.125 mg, respectively, per 200 mg of protein per ml.

The DH, as defined by Adler-Nissen (1986, *Enzymic Hydrolysis of Food Proteins*, Elsevier Applied Science Publishers), was determined by reaction of the supernatant with OPA (ortho-phtaldialdehyde, Sigma Chemical Co., St. Louis, Mo.). For the OPA reagent, 160 mg of OPA was dissolved in 4 ml of ethanol and transferred to a 200 ml volumetric flask containing a solution of 7.62 g of disodium tetraborate decahydrate, 200 mg of sodium dodecylsulphate, and 176 mg of dithiothreitol and the flask was filled to 200 ml with water.

A volume of 25 μl of suitably diluted supernatant was mixed with 200 μl of OPA reagent in a microtiter plate well and allowed to react for exactly 2 minutes at 25° C. The absorbance at 340 nm was measured in a microtiter plate reader and compared to the absorbance of a 95 mM L-serine standard solution after subtraction of the blank value (water reacted with OPA-reagent). To determine the true DH, the serine equivalents measured in the supernatants were corrected with the factors suggested by Adler-Nissen for the trinitrobenzenesulfonic acid method (Adler-Nissen, 1979, *Agricultural and Food Chemistry* 17: 1256) which gave the same response as the described OPA method. The degree of hydrolysis was calculated on basis of the total amount of protein in the hydrolysis mixture (not on basis of soluble protein).

The results showed that dipeptidyl aminopeptidase increased the degree of hydrolysis 5% above the samples with FLAVOURZYME™ and ALCALASE™ alone for all the proteins tested.

Example 16

Increased Protein Solubility and Release of Glutamate by Deamidation

Wheat gluten (WG) was obtained from Cargill (JOB 5141) and deamidated wheat gluten (DWG) was obtained from StaPro Consultancy B.V., Lemdijk 32, 9422 TH Smilde, NL. Suspensions of 8% protein were made by mixing 11 g of gluten with 89 g of water. The pH was adjusted to 6.5 with NaOH. Glutamate/aspartate specific protease (SP446), obtainable as described in WO 91/13554, or lysine/arginine specific protease (SP387) obtainable as described in WO 89/06270, was added to the suspensions. The dosage was 0.01 AU/g protein for SP446 and 0.006 AU/g protein for SP387. FLAVOURZYME™ (an non-specifically acting protease preparation available from Novo Nordisk A/S, Bagsvaerd, Denmark, containing endo- and exo-peptidase activities, and obtained by fermentation of Aspergillus oryzae) was added to some of the hydrolysates at a dosage of 20 LAPU/g protein. One LAPU (Leucine Amino Peptidase Unit) is the amount of enzyme which decomposes 1 micromole of L-leucine-p-nitroanilide per minute under the following conditions: 26 mM L-leucine-p-nitroanilide in 0.1 M Tris pH 8.0 buffer at 40° C. for 10 minutes. Upon hydrolysis, p-nitroanilide is liberated turning the solution yellow which is monitored 405 nm.

The hydrolyses were carried out at 50° C. without further pH adjustment for 18 hours. The enzymes were inactivated by heating at 85° C. for 15 minutes. The pH was adjusted to 5 and the hydrolysates were centrifuged. The content of protein and free glutamate in the supernatant was determined.

The protein content was determined by Kjeldahl analysis, using a Kjeldahl factor of 6.25.

The content of free glutamate was determined by use of a glutamate determination kit according to the manufacturer's instructions (Boehringer-Mannheim, Indianapolis, Ind.). The method was adapted for use in microtiter plates.

When comparing wheat gluten (WG) to deamidated wheat gluten (DWG), the results as shown in Table 4 demonstrated that deamidation increased the susceptibility of the gluten to specific proteases, such that more protein became soluble. By addition of FLAVOURZYME™ with a specific protease, the release of glutamate was doubled due to deamidation.

TABLE 4

| Hydrolysate | Protein Solubility % | | Glutamate Content mg/l | |
|---|---|---|---|---|
| | WG | DWG | WG | DWG |
| SP446 | 18 | 54 | 0 | 0 |
| SP387 | 35 | 44 | 0 | 0 |
| SP446 + FLAVOURZYME ™ | 34 | 87 | 1000 | 2000 |

Example 17

Enzymatic Deamidation and Release of Glutamate

Peptidoglutaminase II was produced by growing Bacillus circulans strain ATCC 21590 in shake flasks (400 ml) containing 200 ml of a medium composed of 1% polypeptone, 0.5% lactose, 0.025% $MgSO_4$-$7H_2O$, 0.005% $FeSO_4$-$7H_2O$, 0.025% $KH_2PO_4$, and 17% $Na_2HPO_4$-$12H_2O$ (pH adjusted to 7.2), at 30° C. for 20 hours with mixing at 270 rpm. The cells were harvested by centrifugation at 4000 rpm in 1 litre flasks. The cells were then frozen.

The purification of peptidoglutaminase II from Bacillus circulans was performed at room temperature. The frozen Bacillus circulans cells were thawed and suspended in Lysis buffer (50 mM Tris/HCI; 25% (w/v) sucrose; 1 mM EDTA, pH 8.0) until a homogeneous suspension was obtained—100 g wet cells per liter of Lysis buffer. Lysozyme (10 mg/ml) and DNAse I (Sigma DN-25, 10 mg/ml) were dissolved in Lysis buffer. Then 100 ml of lysozyme solution, 10 ml of 1.0 M $MgCl_2$, and 1 ml of DNAse I solution were added per litre of cell suspension. The enzymes were allowed to act for 1 hour.

The suspension was filtered through a Seitz depth filter plate and the filtrate was transferred to a 10 mM $KH_2PO_4$/NaOH, pH 8.0 (Buffer A) on a Sephadex G25 column (Pharmacia). The enzyme solution was applied to a SOURCE Q column (Pharmacia) equilibrated in Buffer A and eluted with a linear NaCl gradient (0→500 mM) in Buffer A. Fractions from the column were analysed for Peptidoglutaminase II activity as described below and fractions with activity were pooled. The absorbance of the pooled fractions at 280 nm was 1.78, thus the protein content was estimated to 1.8 mg/ml.

The purity of the protein in the peptidoglutaminase II pool was approximately 25% as judged from a SDS-PAGE gel. Thus, the preparation contained approximately 0.5 mg/ml of pure peptidoglutaminase II.

The peptidoglutaminase activity was determined by measuring the ammonia formed during hydrolysis of γ-carboxyamide of N-tert-Butoxycarbonyl-Gln-Pro (N-t-BOC-Gln-Pro; SIGMA No. B-4403) using the Boehringer-Mannheim kit for ammonia determination (Cat. No. 1112732). In this kit, ammonia is measured by determination of the consumption of NADH by glutamate dehydrogenase, and blanks without the addition of N-t-BOC-Gln-Pro were also applied in order to subtract the effect of other NADH consuming enzymes.

A total of 200 mg of wheat gluten protein was added to 9 ml of boiling water and after cooling, the pH was adjusted to 7.0. Then 250 µl of the peptidoglutaminase II preparation (PEP) described above was added. The glutamate/aspartate specific protease (SP446) described in Example 16 was added in an amount of 0.04 AU/g protein, and FLAVOURZYME™ described in Example 16 was added in an amount of 20 LAPU/g protein.

Hydrolysis was allowed to proceed without pH adjustment for 18 hours at 50° C. Controls without the addition of peptidoglutarninase were also run. The hydrolysates were centrifuged and glutamate was measured as described in Example 16. The DH was determined as described in Example 15.

The results as shown below in Table 5 demonstrated that hydrolysis with the peptidoglutaminase preparation increased the DH as well as the release of glutamate.

TABLE 5

| Hydrolysis | DH % | Glutamate mg/l |
|---|---|---|
| Minus PEP | 40 | 131 |
| Plus PEP | 43 | 171 |

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli DH5α pMWR52 | NRRL B-21682 | Apr. 18, 1997 |

What is claimed is:

1. An isolated polypeptide having dipeptidyl aminopeptidase activity, selected from the group consisting of:
    (a) a polypeptide having an amino acid sequence which has at least 95% identity with amino acids 17 to 771 of SEQ ID NO:2;
    (b) a polypeptide which is encoded by a nucleic acid sequence which hybridizes under high stringency conditions with (i) nucleotides 49 to 2396 of SEQ ID NO. 1, or (ii) the cDNA sequence corresponding to nucleotides 49 to 2396 of SEQ ID NO. 1, wherein high stringency conditions are defined as prehybridization and hybridization at 42° C. in 5×SSPE, 0.3% SDS, 200 µg/ml sheared and denatured salmon sperm DNA, and 50% formamide, and washing with 2×SSC, 0.2% SDS at 65° C.; and
    (c) a fragment of (a) or (b) wherein the fragment has dipeptidyl aminopeptidase activity.

2. The polypeptie of claim 1 comprising an amino acid sequence which has at least 95% identity with amino acias 17 to 771 of SEQ ID NO:2.

3. The polypeptide of claim 2, comprsing an amino acid sequence which has at least 97% identity with amino acids 17 to 771 of SEQ ID NO:2.

4. The polypeptide of cliam 1, comprising tne amino acid sequence of SEQ ID NO:2.

5. The potypeptide of claim 1, consisting of tne amino acid sequence of SEQ ID NO:2 or a fragment thereof having dipeptidyl aminopeptidase activity.

6. The polypeptide of claim 5, consisting of the amino acid sequence of SEQ ID NO:2.

7. The polypeptide of claim 6, consisting of amino acids 17 to 771 of SEQ ID NO:2.

8. The polypeptide of claim 2, which is obtained from an Aspergillus strain.

9. The polypeptide of claim 8, which is obtained from an *Aspergillus oryzae* strain.

10. The polypeptide of claim 1, which is encoded by a nucleic acid sequence which hybridizes under high stringency conditions with (i) nucleotides 49 to 2396 of SEQ ID NO. 1, or (ii) the cDNA sequence corresponding to nuclotides 49 to 2396 of SEQ ID NO. 1, wherein high stringency conditions are defined as prehybridization and hybridization at 42° C. in 5×SSPE, 0.3% SDS, 200 µg/ml sheared and denatured salmon sperm DNA, and 50% formamide, and washing with 2×SSC, 0.2% SDS at 65° C.

11. The polypeptide of claim 10, which is obtained from an Aspergillus strain.

12. The polypeptide of claim 12, which is obtained from an *Aspergillus oryzae* strain.

13. The polypeptide of claim 1, which is encoded by the nucleic acid sequence contained in plasmia pMWR52 which is contained in *E. coli* NRRL B-21682.

14. The polypeptide of claim 1, which acts synergistically with an aminopeptidase to hydrolyze a polypeptide.

15. An isolated polypeptide having dipeptidyl aminopeptidase activity from an Aspergillus strain, having the following physicochemical properties: (a) a pH optimum at about pH 8.7 determined after incubation for 5 minutes at ambient temperature in the presence of 2.9 mM Ala-Pro-para-nitroanilide; (b) a temperature stability of 90% or more, relative to initial activity, after incubation for 20 minutes at 65° C. pH 7.5 in the absence of substrate, wherein remaining activity was determined with 2.9 mM Ala-Pro-para-nitroanilide in 50 mM sodium phosphate pH 7.5; (c) activity towards Xaa-Pro-para-nitroanilide or Xaa-Ala-para-nitroanilide at ambient temperature in 50 mM sodium phosphate pH 7.5, wherein Xaa is selected from the group consisting of Ala, Arg, Asp, Gly, and Val; and (d) a molecular weight of about 93–96 kDa by SDS-PAGE.

16. The polypeptide of claim 15, which is obtained from an *Aspergillus oryzae* strain.

17. A flavor-improving composition comprising a polypeptide of claim 1 and a suitable carrier.

18. A pre-mix for a dough comprising a polypeptide of claim 1 and a baking ingredient.

19. An isolated nucleic acid sequence encoding a polypeptide having dipeptidyl aminopeptidase activity, selected from the group consisting of:
    (a) a nucleic acid sequence encoding a polypeptide having an amino acid sequence which has at least 95% identity with amino acids 17 to 771 of SEQ ID NO:2;
    (b) a nucleic acid sequence which hybridizes under high stringency conditions with (i) nucleotides 49 to 2396 of SEQ ID NO. 1, or (ii) the cDNA sequence corresponding to nucleotides 49 to 2396 of SEQ ID NO. 1, wherein high stringency conditions are defined as prehybridization and hybridization at 42° C. in 5×SSPE, 0.3% SDS, 200 µg/ml sheared and denatures salmon sperm DNA, and 50% formamide, and washing with 2×SSC, 0.2% SDS at 65° C.; and
    (c) a nucleic acid fragment of (a) or (b), which encodes a polypeptide having dipeptidyl aminopeptidase activity.

20. The nucleic acid sequenc of claim 19, which is obtained from an Aspergillus strain.

21. The nucleic acid sequence of claim 20, which is obtained from an *Aspergillus oryzae* strain.

22. The nucleic acid sequence of claim 19, which is encoded by the nucleic acid sequence contained in plasmid pMWR52 which is contained in *E. coli* NRRL B-21682.

23. A nucleic acid construct comprising the nucleic acid sequence of claim 19 operably linked to one or more control sequences wnich direct tne production of the poypeptide in a suitable expression host.

24. A recombinant expression vector comprising the nucleic acid construct of claim 23, a promoter, and transcriptional and translational stop signals.

25. A recombinant host cell comprising the nucleic acid construct of claim 23.

26. A method for producing a polypeptie having dipeptidyl aminopeptidase activity comprising (a) cultivating the host cell of claim 25 under conditions suitable for production of the polypeptide; and (b) recovering the polypeptide.

* * * * *

```
                        SEQUENCE LISTING

<160> NUMBER OF SEQ ID NOS: 13

<210> SEQ ID NO 1
<211> LENGTH: 4280
<212> TYPE: DNA
<213> ORGANISM: Aspergillus

<400> SEQUENCE: 1
aatttcctca ctcatccttc tatccaccgc caaaatgaag gccgctaccc tcctctctct    60
tctgagcgtt accggactcg tcgccgctgc tccagctggc aacggtacgt atcctgaacg   120
acaatgtaag acgcttgact gatgattagt aggcccagct ggtggaatca tcgaccgcga   180
tcttcccgtc cctgtccctg gactccctac caagggtctc cctattgttg acggattgac   240
tggcggcaat aagggtggcg agaagcctgg aagcaaggtt actcctcgtg aagaccctac   300
cggcagcgcc cctgatggca agggcaatga tggccccgac ggtgatctta ccggacgtcc   360
cggtcaaggg ggtcttgaca acccttttcga tctccctact ccagagcttc ctcccgtcaa   420
gcttcctggc ggacttgacg gtggcaaggg cggtctcggc cttcgtcgtc gtggcagccc   480
agtagacggt ctccctgtcg ttgggcctgt tgttggtggt gttctaggtg gcggtggtgc   540
tggcagtggt gctggtgcca agggtggtgc tggtagtggt accgttgggc gtcgtggcag   600
cccagtagac ggtctccctg ttgttgggcc tgttgttggt ggtgtcctag gtggcggtgg   660
tgctggcagt ggtgctggtg ccaagggtgg tgctggtagt ggtaccccta agcgccgtga   720
cggtccagtg gacggtgttc ctgtcgttgg agagcttgct gaaggtgcta ctggaggtct   780
tctaggtggt gatgctggtt ctgctgatgc tgctggtgct gatgctggtg ctgatgctgg   840
tgctggtgct ggtgggcaat agtctaacaa gggctttacg gcatcaatgt gaggttatcc   900
aacatccatc cttggtggcc attcgtaaat agcaacaaag agggtggta cttggtcgcg   960 atgtcattgc tcctgcgatt gaagctagcg attcctgtat gtacaataat tttaagcacg  1020
cttggttcca tactgtttct tcactggttt ttggatattt tttcacttat tgaatcttgt  1080
agtagtccag cttctcatgg ttagacacgg gataaccccc caatagcatc atctgcaggt  1140
ttgatgttgc aatggtcaag ttttgtctta aattatgtac gagtcttggg ttacaccgct  1200
agaagctttg ccaccaatga agctgtagct tgtccaacgg ctatcagcgg ttttttttat  1260
gagaatcttg gcaggatagg aaaagttggt ggtggtgaag gagctaatgc aggaggtgga  1320
gtgactgata agacgcgatt tctgcgggga aaagaaaaa ggaccaattt atgggactat  1380
ttatttaaac gggaagtctt caattccgct tcgccagcca tcccttgatt cgagctgaac  1440
tcggggtttt ttccaccatg aaggtacgtc aattccactg attaaacatt atttgttaca  1500
tacactccat cattgagtca attataatta acacctcata attcagtact ccaagcttct  1560
```

-continued

```
gctgctcctg gtcagtgtgg tccaggccct ggatgtgcct cggaaaccac acgcgcccac    1620
cggagaaggc agtaagcgtc tcaccttcaa tgagaccgta gtcaagcaag caattacgcc    1680
gacctctcgc tcggtgcaat ggctctcggg cgcagaggat ggatcctacg tgtacgcggc    1740
ggaagacggc agtctcacca tcgagaacat cgtcaccaac gagtcacgca cgctcatccc    1800
tgcggacaag attccgacag ggaaggaagc gttcaattac tggatccatc ccgacttgtc    1860
gtcggtgctg tgggcgtcca accacaccaa gcagtatcgg cattcgttct tgccgatta    1920 ttacgtccag gatgtggagt cactcaagtc cgtgcccctg atgcccgatc aggaaggtga    1980
tattcaatat gcccaatgga gccccgtggg caataccatc gcttttgttc gcgagaatga    2040
cctttatgtc tgggataatg gtaccgttac tcgcattact gatgatggtg gccccgacat    2100
gttccacggc gtgccggact ggatctatga agaggagatc ctcggcgatc gctacgcgtt    2160
gtggttctcg ccagatggtg aatatctggc ttacttgagc ttcaatgaga ctggggttcc    2220
gacctacacc gttcagtatt atatggataa ccaagagatc gctccggcgt atccatggga    2280
gctgaagata aggtatccca aggtgtcgca gacgaatccg accgtgacgt tgagtctgct    2340
taacatcgct agcaaggagg tgaagcaggc gccgatcgac gcgttcgagt caactgactt    2400
gatcattggc gaggttgctt ggctcactga tactcacacc accgttgctg ctaaggcgtt    2460
caaccgtgtc caggaccagc aaaaggtcgt cgcggtcgat actgcctcga caaggctac    2520 tgtcatcagc gaccgagatg ggaccgatgg atggctcgat aaccttcttt caatgaagta    2580
tattggccct atcaagccgt ccgacaagga tgcctactac atcgacatct ctgaccattc    2640
gggatgggcg catctgtatc tcttccccgt ttcgggcggc gaacctatcc cactaaccaa    2700
aggcgactgg gaggtcacgt ctattctgag tattgatcag gaacgccagt tggtgtacta    2760
cctgtcgact caacaccaca gcaccgagcg ccatctctac tccgtctcct attccacgtt    2820
tgcggtcacc ccgtcgtcg acgacaccgt tgccgcgtac tggtctgctt ccttctccgc    2880
gaactcgggc tactacatcc tcacatacgg aggcccagac gtaccctacc aggaactcta    2940
cacgaccaac agtaccaaac cactccgcac aatcaccgac aacgccaaag tactcgagca    3000
aatcaaggac tatgcattgc ccaacatcac ctacttcgag cttcccctcc cctccggaga    3060
aaccctcaat gtgatgcagc gcttaccccc cgggttctcc ccggataaga agtaccccat    3120
acttttcacc ccatacggcg gcccaggcgc ccaagaagtg accaagagat ggcaagccct    3180
gaatttcaag gcctatgtcg cctccgacag cgaactcgag tacgtaaccct ggactgtcga    3240 caaccgcggc acaggtttca aggacgcaa gttccgctcc gccgtcacgc gccaactcgg    3300
cctcctcgaa gcagaagacc agatctacgc cgcgcaacag gcggccaaca tcccctggat    3360
cgatgcagac cacatcggca tctggggctg gagtttcgga ggctacttga ccagcaaggt    3420
cctggagaag gacagcggtg ctttcacatt aggagtcatc accgcccctg tttctgactg    3480
gcgtttctac gactcaatgt acacggagcg ctacatgaag accctctcga ccaatgagga    3540
gggctacgag accagcgccg tccgcaagac tgacgggttc aagaacgtcg agggcggatt    3600
cttgatccag cacggaacgg cgacgataa cgtccatttc cagaactcgg ctgcgctggt    3660
ggatctcctg atgggcgatg gcgtctctcc tgagaagctc cattcgcaat ggttcacaga    3720
ctcagaccac ggaatcagct accatggtgg cggcgtgttc ctgtacaagc aactggcccg    3780
gaagctctac caggagaaga accgacagac gcaggtgctg atgcaccagt ggactaagaa    3840
ggacttggag gagtagaagc ggcacatcat tcattcattt taaagcgact ggctacacat    3900
agcatacata gcaattgata cttcgtattt taccctcccc acagccacga ccatcaccca    3960
```

```
ttggcgcaaa attctccccg caccataaac tagcgcgacg aggctgaaaa tctgccagaa    4020
atctacttaa agctcgtgtt ggcccagtcc ctcacaaccc aaaccatccc aagtaaacaa    4080
aaccaaaaaa aaatcccata gaaaatggcc gacatcccca ctcaacagtc caaatcacaa    4140
ccctccccac caaatccgta acaatcaccc cgcaacgagc gaccatcgtt cgcgagatac    4200
acacctccat ccaggtatgc acataccacc tcacctgacc atccaaccct acttacagtc    4260
aacgtaaact aacaaaattc                                                4280
```

<210> SEQ ID NO 2
<211> LENGTH: 771
<212> TYPE: PRT
<213> ORGANISM: Aspergillus oryzae

<400> SEQUENCE: 2

```
Met Lys Tyr Ser Lys Leu Leu Leu Leu Val Ser Val Val Gln Ala
 1               5                  10                  15

Leu Asp Val Pro Arg Lys Pro His Ala Pro Thr Gly Glu Gly Ser Lys
                20                  25                  30

Arg Leu Thr Phe Asn Glu Thr Val Lys Gln Ala Ile Thr Pro Thr
            35                  40                  45

Ser Arg Ser Val Gln Trp Leu Ser Gly Ala Glu Asp Gly Ser Tyr Val
    50                  55                  60

Tyr Ala Ala Glu Asp Gly Ser Leu Thr Ile Glu Asn Ile Val Thr Asn
65                  70                  75                  80

Glu Ser Arg Thr Leu Ile Pro Ala Asp Lys Ile Pro Thr Gly Lys Glu
                85                  90                  95

Ala Phe Asn Tyr Trp Ile His Pro Asp Leu Ser Ser Val Leu Trp Ala
            100                 105                 110

Ser Asn His Thr Lys Gln Tyr Arg His Ser Phe Phe Ala Asp Tyr Tyr
        115                 120                 125

Val Gln Asp Val Glu Ser Leu Lys Ser Val Pro Leu Met Pro Asp Gln
    130                 135                 140

Glu Gly Asp Ile Gln Tyr Ala Gln Trp Ser Pro Val Gly Asn Thr Ile
145                 150                 155                 160

Ala Phe Val Arg Glu Asn Asp Leu Tyr Val Trp Asp Asn Gly Thr Val
                165                 170                 175

Thr Arg Ile Thr Asp Asp Gly Gly Pro Asp Met Phe His Gly Val Pro
            180                 185                 190

Asp Trp Ile Tyr Glu Glu Glu Ile Leu Gly Asp Arg Tyr Ala Leu Trp
        195                 200                 205

Phe Ser Pro Asp Gly Glu Tyr Leu Ala Tyr Leu Ser Phe Asn Glu Thr
    210                 215                 220

Gly Val Pro Thr Tyr Thr Val Gln Tyr Tyr Met Asp Asn Gln Glu Ile
225                 230                 235                 240

Ala Pro Ala Tyr Pro Trp Glu Leu Lys Ile Arg Tyr Pro Lys Val Ser
                245                 250                 255

Gln Thr Asn Pro Thr Val Thr Leu Ser Leu Leu Asn Ile Ala Ser Lys
            260                 265                 270

Glu Val Lys Gln Ala Pro Ile Asp Ala Phe Glu Ser Thr Asp Leu Ile
        275                 280                 285

Ile Gly Glu Val Ala Trp Leu Thr Asp Thr His Thr Val Ala Ala
    290                 295                 300

Lys Ala Phe Asn Arg Val Gln Asp Gln Gln Lys Val Val Ala Val Asp
305                 310                 315                 320
```

-continued

```
Thr Ala Ser Asn Lys Ala Thr Val Ile Ser Asp Arg Asp Gly Thr Asp
                325                 330                 335
Gly Trp Leu Asp Asn Leu Leu Ser Met Lys Tyr Ile Gly Pro Ile Lys
            340                 345                 350
Pro Ser Asp Lys Asp Ala Tyr Tyr Ile Asp Ile Ser Asp His Ser Gly
        355                 360                 365
Trp Ala His Leu Tyr Leu Phe Pro Val Ser Gly Glu Pro Ile Pro
370                 375                 380
Leu Thr Lys Gly Asp Trp Glu Val Thr Ser Ile Leu Ser Ile Asp Gln
385                 390                 395                 400
Glu Arg Gln Leu Val Tyr Tyr Leu Ser Thr Gln His His Ser Thr Glu
                405                 410                 415
Arg His Leu Tyr Ser Val Ser Tyr Ser Thr Phe Ala Val Thr Pro Leu
            420                 425                 430
Val Asp Asp Thr Val Ala Ala Tyr Trp Ser Ala Ser Phe Ser Ala Asn
        435                 440                 445
Ser Gly Tyr Tyr Ile Leu Thr Tyr Gly Gly Pro Asp Val Pro Tyr Gln
    450                 455                 460
Glu Leu Tyr Thr Thr Asn Ser Thr Lys Pro Leu Arg Thr Ile Thr Asp
465                 470                 475                 480
Asn Ala Lys Val Leu Glu Gln Ile Lys Asp Tyr Ala Leu Pro Asn Ile
                485                 490                 495
Thr Tyr Phe Glu Leu Pro Leu Pro Ser Gly Glu Thr Leu Asn Val Met
            500                 505                 510
Gln Arg Leu Pro Pro Gly Phe Ser Pro Asp Lys Lys Tyr Pro Ile Leu
        515                 520                 525
Phe Thr Pro Tyr Gly Gly Pro Gly Ala Gln Glu Val Thr Lys Arg Trp
    530                 535                 540
Gln Ala Leu Asn Phe Lys Ala Tyr Val Ala Ser Asp Ser Glu Leu Glu
545                 550                 555                 560
Tyr Val Thr Trp Thr Val Asp Asn Arg Gly Thr Gly Phe Lys Gly Arg
                565                 570                 575
Lys Phe Arg Ser Ala Val Thr Arg Gln Leu Gly Leu Leu Glu Ala Glu
            580                 585                 590
Asp Gln Ile Tyr Ala Ala Gln Ala Ala Asn Ile Pro Trp Ile Asp
        595                 600                 605
Ala Asp His Ile Gly Ile Trp Gly Trp Ser Phe Gly Gly Tyr Leu Thr
    610                 615                 620
Ser Lys Val Leu Glu Lys Asp Ser Gly Ala Phe Thr Leu Gly Val Ile
625                 630                 635                 640
Thr Ala Pro Val Ser Asp Trp Arg Phe Tyr Asp Ser Met Tyr Thr Glu
                645                 650                 655
Arg Tyr Met Lys Thr Leu Ser Thr Asn Glu Glu Gly Tyr Glu Thr Ser
            660                 665                 670
Ala Val Arg Lys Thr Asp Gly Phe Lys Asn Val Glu Gly Gly Phe Leu
        675                 680                 685
Ile Gln His Gly Thr Gly Asp Asp Asn Val His Phe Gln Asn Ser Ala
    690                 695                 700
Ala Leu Val Asp Leu Leu Met Gly Asp Gly Val Ser Pro Glu Lys Leu
705                 710                 715                 720
His Ser Gln Trp Phe Thr Asp Ser Asp His Gly Ile Ser Tyr His Gly
                725                 730                 735
```

-continued

```
Gly Gly Val Phe Leu Tyr Lys Gln Leu Ala Arg Lys Leu Tyr Gln Glu
            740                 745                 750
Lys Asn Arg Gln Thr Gln Val Leu Met His Gln Trp Thr Lys Lys Asp
        755                 760                 765
Leu Glu Glu
    770

<210> SEQ ID NO 3
<211> LENGTH: 20
<212> TYPE: PRT
<213> ORGANISM: Aspergillus oryzae
<220> FEATURE:
<223> OTHER INFORMATION: Xaa = Any aminoacid
<221> NAME/KEY: VARIANT
<222> LOCATION: (1)...(20)
<223> OTHER INFORMATION: Xaa = Any Amino Acid
<221> NAME/KEY: VARIANT
<222> LOCATION: (1)...(20)
<223> OTHER INFORMATION: Xaa = Any Amino Acid

<400> SEQUENCE: 3

Xaa Glu Gly Ser Lys Arg Leu Thr Phe Xaa Glu Thr Val Val Lys Gln
  1               5                  10                  15
Ala Ile Thr Pro
            20

<210> SEQ ID NO 4
<211> LENGTH: 22
<212> TYPE: PRT
<213> ORGANISM: Aspergillus oryzae

<400> SEQUENCE: 4

Gln Arg Leu Pro Pro Gly Phe Ser Pro Asp Lys Lys Tyr Pro Ile Leu
  1               5                  10                  15
Phe Thr Pro Tyr Gly Gly
            20

<210> SEQ ID NO 5
<211> LENGTH: 7
<212> TYPE: PRT
<213> ORGANISM: Aspergillus oryzae

<400> SEQUENCE: 5

Lys Tyr Ile Gly Pro Ile Lys
  1               5

<210> SEQ ID NO 6
<211> LENGTH: 7
<212> TYPE: PRT
<213> ORGANISM: Aspergillus oryzae

<400> SEQUENCE: 6

Gly Glu Gly Ser Lys Arg Leu
  1               5

<210> SEQ ID NO 7
<211> LENGTH: 8
<212> TYPE: PRT
<213> ORGANISM: Aspergillus oryzae
<220> FEATURE:
<223> OTHER INFORMATION: Xaa = Any aminoacid
<221> NAME/KEY: VARIANT
<222> LOCATION: (1)...(8)
<223> OTHER INFORMATION: Xaa = Any Amino Acid
<221> NAME/KEY: VARIANT
<222> LOCATION: (1)...(8)
```

-continued

<223> OTHER INFORMATION: Xaa = Any Amino Acid

<400> SEQUENCE: 7

Xaa Pro Ile Leu Phe Thr Pro Tyr
1               5

<210> SEQ ID NO 8
<211> LENGTH: 16
<212> TYPE: PRT
<213> ORGANISM: Aspergillus oryzae
<220> FEATURE:
<223> OTHER INFORMATION: Xaa = Any aminoacid
<221> NAME/KEY: VARIANT
<222> LOCATION: (1)...(16)
<223> OTHER INFORMATION: Xaa = Any Amino Acid
<221> NAME/KEY: VARIANT
<222> LOCATION: (1)...(16)
<223> OTHER INFORMATION: Xaa = Any Amino Acid

<400> SEQUENCE: 8

Xaa Val Pro Leu Met Pro Asp Gln Gln Gly Asp Ile Gln Tyr Ala Gln
1               5                   10                  15

<210> SEQ ID NO 9
<211> LENGTH: 21
<212> TYPE: PRT
<213> ORGANISM: Aspergillus oryzae

<400> SEQUENCE: 9

Gly Ala Tyr Thr Gly Gly Ile Thr Ile Thr Ala Tyr Gly Ala Arg Gly
1               5                   10                  15

Ala Arg Gly Ala Arg
            20

<210> SEQ ID NO 10
<211> LENGTH: 32
<212> TYPE: PRT
<213> ORGANISM: Aspergillus oryzae

<400> SEQUENCE: 10

Gly Gly Arg Thr Ala Tyr Thr Thr Tyr Thr Thr Arg Thr Cys Ile Gly
1               5                   10                  15

Gly Ile Ser Trp Arg Ala Ala Ile Cys Cys Ile Gly Gly Ile Gly Gly
            20                  25                  30

<210> SEQ ID NO 11
<211> LENGTH: 931
<212> TYPE: PRT
<213> ORGANISM: Saccharomyces cerevisiae

<400> SEQUENCE: 11

Met Ser Ala Ser Thr His Ser His Lys Arg Lys Asn Ser His Leu Phe
1               5                   10                  15

Pro Gln Arg Lys Ser Ser Asn Ser Ser Met Asp Lys Pro Phe Phe Pro
                20                  25                  30
Asn Asn Asp Ser Val Ala Asn Thr Asp Pro Gln Ser Asn Glu Asn Gly
            35                  40                  45

His Thr Ile Asn Glu Ile Arg Pro Thr Glu Ala Thr Ile Asp Val Thr
        50                  55                  60

Asp Val Pro Gln Thr Pro Phe Leu Gln Glu Gln Tyr Ser Met Arg Pro
65                  70                  75                  80

Arg Arg Glu Ser Phe Gln Phe Asn Asp Ile Glu Asn Gln His His Thr
                85                  90                  95

```
His Ser Phe Phe Ser Val Asn Lys Phe Asn Arg Arg Trp Gly Glu Trp
            100                 105                 110
Ser Leu Pro Glu Lys Arg Ser Tyr Val Leu Val Phe Thr Leu Ile Ala
        115                 120                 125
Leu Ser Val Leu Val Leu Leu Val Ile Leu Ile Pro Ser Lys Leu Leu
    130                 135                 140
Pro Thr Lys Ile Thr Arg Pro Lys Thr Ser Ala Gly Asp Ser Ser Leu
145                 150                 155                 160
Gly Lys Arg Ser Phe Ser Ile Glu Asn Val Leu Asn Gly Asp Phe Ala
                165                 170                 175
Ile Pro Glu Asp Thr Phe His Phe Ile Asp Pro Pro Gln Arg Leu Leu
            180                 185                 190
Gly Gln Asp Ser Asp Pro Gly Leu Tyr Phe Thr Thr Lys Glu Ile Asp
        195                 200                 205
Gly His Thr Asn Phe Ile Ala Lys Gln Leu Phe Asp Glu Thr Phe Glu
    210                 215                 220
Val Asn Leu Gly Gly Asn Arg Phe Leu Tyr Glu Gly Val Glu Phe Thr
225                 230                 235                 240
Val Ser Thr Val Gln Ile Asn Tyr Lys Leu Asp Lys Leu Ile Phe Gly
                245                 250                 255
Thr Asn Leu Glu Ser Glu Phe Arg His Ser Ser Lys Gly Phe Tyr Trp
            260                 265                 270
Ile Lys Asp Leu Asn Thr Gly Asn Ile Glu Pro Ile Leu Pro Pro Glu
        275                 280                 285
Lys Ser Asp Asp Asn Tyr Glu Leu Gly Leu Ser Lys Leu Ser Tyr Ala
    290                 295                 300
His Phe Ser Pro Ala Tyr Asn Tyr Ile Tyr Phe Val Tyr Glu Asn Asn
305                 310                 315                 320
Leu Phe Leu Gln Gln Val Asn Ser Gly Val Ala Lys Lys Val Thr Glu
                325                 330                 335
Asp Gly Ser Lys Asp Ile Phe Asn Ala Lys Pro Asp Trp Ile Tyr Glu
            340                 345                 350
Glu Glu Val Leu Ala Ser Asp Gln Ala Ile Trp Trp Ala Pro Asp Asp
        355                 360                 365
Ser Lys Ala Val Phe Ala Arg Phe Asn Asp Thr Ser Val Asp Asp Ile
    370                 375                 380
Arg Leu Asn Arg Tyr Thr Asn Met Asn Glu Ala Tyr Leu Ser Asp Thr
385                 390                 395                 400
Lys Ile Lys Tyr Pro Lys Pro Gly Phe Gln Asn Pro Gln Phe Asp Leu
                405                 410                 415
Phe Leu Val Asn Leu Gln Asn Gly Ile Ile Tyr Ser Ile Asn Thr Gly
            420                 425                 430
Gly Gln Lys Asp Ser Ile Leu Tyr Asn Gly Lys Trp Ile Ser Pro Asp
        435                 440                 445
Thr Phe Arg Phe Glu Ile Thr Asp Arg Asn Ser Lys Ile Leu Asp Val
    450                 455                 460
Lys Val Tyr Asp Ile Pro Ser Ser Gln Met Leu Thr Val Arg Asn Thr
465                 470                 475                 480
Asn Ser Asn Leu Phe Asn Gly Trp Ile Glu Lys Thr Lys Asp Ile Leu
                485                 490                 495
Ser Ile Pro Pro Lys Pro Glu Leu Lys Arg Met Asp Tyr Gly Tyr Ile
            500                 505                 510
Asp Ile His Ala Asp Ser Arg Gly Phe Ser His Leu Phe Tyr Tyr Pro
```

```
            515                 520                 525
Thr Val Phe Ala Lys Glu Pro Ile Gln Leu Thr Lys Gly Asn Trp Glu
            530                 535                 540
Val Thr Gly Asn Gly Ile Val Gly Tyr Glu Tyr Glu Thr Asp Thr Ile
545                 550                 555                 560
Phe Phe Thr Ala Asn Glu Ile Gly Val Met Ser Gln His Leu Tyr Ser
                565                 570                 575
Ile Ser Leu Thr Asp Ser Thr Thr Gln Asn Thr Phe Gln Ser Leu Gln
            580                 585                 590
Asn Pro Ser Asp Lys Tyr Asp Phe Tyr Asp Phe Glu Leu Ser Ser Ser
            595                 600                 605
Ala Arg Tyr Ala Ile Ser Lys Lys Leu Gly Pro Asp Thr Pro Ile Lys
610                 615                 620
Val Ala Gly Pro Leu Thr Arg Val Leu Asn Val Ala Glu Ile His Asp
625                 630                 635                 640
Asp Ser Ile Leu Gln Leu Thr Lys Asp Glu Lys Phe Lys Glu Lys Ile
            645                 650                 655
Lys Asn Tyr Asp Leu Pro Ile Thr Ser Tyr Lys Thr Met Val Leu Asp
            660                 665                 670
Asp Gly Val Glu Ile Asn Tyr Ile Glu Ile Lys Pro Ala Asn Leu Asn
            675                 680                 685
Pro Lys Lys Lys Tyr Pro Ile Leu Val Asn Ile Tyr Gly Gly Pro Gly
            690                 695                 700
Ser Gln Thr Phe Thr Thr Lys Ser Ser Leu Ala Phe Glu Gln Ala Val
705                 710                 715                 720
Val Ser Gly Leu Asp Val Ile Val Leu Gln Ile Glu Pro Arg Gly Thr
                725                 730                 735
Gly Gly Lys Gly Trp Ser Phe Arg Ser Trp Ala Arg Glu Lys Leu Gly
                740                 745                 750
Tyr Trp Glu Pro Arg Asp Ile Thr Glu Val Thr Lys Lys Phe Ile Gln
                755                 760                 765
Arg Asn Ser Gln His Ile Asp Glu Ser Lys Ile Ala Ile Trp Gly Trp
            770                 775                 780
Ser Tyr Gly Gly Phe Thr Ser Leu Lys Thr Val Glu Leu Asp Asn Gly
785                 790                 795                 800
Asp Thr Phe Lys Tyr Ala Met Ala Val Ala Pro Val Thr Asn Trp Thr
                805                 810                 815
Leu Tyr Asp Ser Val Tyr Thr Glu Arg Tyr Met Asn Gln Pro Ser Glu
                820                 825                 830
Asn His Glu Gly Tyr Phe Glu Val Ser Thr Ile Gln Asn Phe Lys Ser
            835                 840                 845
Phe Glu Ser Leu Lys Arg Leu Phe Ile Val His Gly Thr Phe Asp Asp
850                 855                 860
Asn Val His Ile Gln Asn Thr Phe Arg Leu Val Asp Gln Leu Asn Leu
865                 870                 875                 880
Leu Gly Leu Thr Asn Tyr Asp Met His Ile Phe Pro Asp Ser Asp His
                885                 890                 895
Ser Ile Arg Tyr His Asn Ala Gln Arg Ile Val Phe Gln Lys Leu Tyr
            900                 905                 910
Tyr Trp Leu Arg Asp Ala Phe Ala Glu Arg Phe Asp Asn Thr Glu Val
            915                 920                 925
Leu His Leu
    930
```

-continued

```
<210> SEQ ID NO 12
<211> LENGTH: 36
<212> TYPE: DNA
<213> ORGANISM: Aspergillus oryzae

<400> SEQUENCE: 12
gatttaaatc accatgaagg tacgtcaatt ccactg                              36

<210> SEQ ID NO 13
<211> LENGTH: 36
<212> TYPE: DNA
<213> ORGANISM: Aspergillus oryzae

<400> SEQUENCE: 13
gttaattaat ctactcctcc aagtccttct tagtcc                              36
```